(12) United States Patent
Murphy et al.

(10) Patent No.: US 11,607,391 B2
(45) Date of Patent: Mar. 21, 2023

(54) MINERAL-COATED MICROSPHERES

(75) Inventors: William L. Murphy, Madison, WI (US); Leenaporn Jongpaiboonkit, Madison, WI (US)

(73) Assignee: TRS HOLDINGS LLC, Ann Arbor, MI (US)

( * ) Notice: Subject to any disclaimer, the term of this patent is extended or adjusted under 35 U.S.C. 154(b) by 1198 days.

(21) Appl. No.: 13/879,178

(22) PCT Filed: Sep. 25, 2009

(86) PCT No.: PCT/US2009/058419
§ 371 (c)(1),
(2), (4) Date: Feb. 18, 2014

(87) PCT Pub. No.: WO2010/036919
PCT Pub. Date: Apr. 1, 2010

(65) Prior Publication Data
US 2014/0161886 A1    Jun. 12, 2014

Related U.S. Application Data

(60) Provisional application No. 61/100,062, filed on Sep. 25, 2008.

(51) Int. Cl.
| | | |
|---|---|---|
| *A61K 9/50* | (2006.01) | |
| *A61K 31/19* | (2006.01) | |
| *A61K 35/02* | (2015.01) | |
| *C12N 15/87* | (2006.01) | |
| *A61K 38/00* | (2006.01) | |

(52) U.S. Cl.
CPC ............ *A61K 9/501* (2013.01); *A61K 9/5031* (2013.01); *A61K 31/19* (2013.01); *A61K 35/02* (2013.01); *C12N 15/87* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,210,715 B1 * | 4/2001 | Starling | B01J 20/28021 424/489 |
| 6,471,993 B1 | 10/2002 | Shastri et al. | |
| 6,541,022 B1 | 4/2003 | Murphy et al. | |
| 6,743,779 B1 | 6/2004 | Unger et al. | |
| 6,767,928 B1 | 7/2004 | Murphy et al. | |
| 2002/0155144 A1 * | 10/2002 | Troczynski | A61K 9/0024 424/423 |
| 2004/0023852 A1 * | 2/2004 | Roberts | A61K 31/715 424/78.01 |
| 2004/0052865 A1 | 3/2004 | Gower et al. | |
| 2005/0249697 A1 * | 11/2005 | Uhrich | A61K 9/1647 424/78.37 |
| 2006/0067969 A1 * | 3/2006 | Lu | A61L 27/3839 424/423 |
| 2007/0059437 A1 * | 3/2007 | Murphy | A61L 27/00 427/2.26 |
| 2008/0090760 A2 | 4/2008 | Hembrough et al. | |
| 2008/0095817 A1 | 4/2008 | Murphy | |
| 2008/0095820 A1 * | 4/2008 | Kumta | C01B 25/324 424/423 |

FOREIGN PATENT DOCUMENTS

| | | |
|---|---|---|
| JP | 2004-530675 | 10/2004 |
| WO | WO 2002/085330 | 10/2002 |
| WO | 2004/085998 A2 | 10/2004 |
| WO | WO 2004/085998 | 10/2004 |
| WO | WO 2008/070355 | 6/2008 |
| WO | WO 2008/082766 | 7/2008 |

OTHER PUBLICATIONS

Jabbarzadeh et al., Apatite nano-crystalline surface modification of poly(lactide-co-glycolide) sintered microsphere scaffolds for bone tissue engineering: implications for protein adsorption, Journal of Biomaterials Science Polymer Edition, 2007, pp. 1141-1152, vol. 18, No. 9 (cited in Oct. 1, 14 IDS, reference.*
Akhtar et al., Antisense oligonucleotide delivery to cultured macrophages is improved by incorporation into sustained-release biodegradable polymer microspheres, Int. J. Pharm., 1997, pp. 57-67, vol. 151.
Bajpai et al., Study of biomineralization of poly(vinyl alcohol)-based scaffolds using an alternate soaking approach, Polymer International, 2007, pp. 557-568, vol. 56, No. 4.
Baron, Molecular Mechanisms of Bone Resorption by the Osteoclast, Anat. Rec., 1989, pp. 317-324, vol. 224.
Barrere et al., Nano-scale study of the nucleation and growth of calcium phosphate coating on titanium implants, Biomaterials, 2004, pp. 2901-2910, vol. 25, No. 14.
Berchane et al., About mean diameter and size distributions of poly(lactide-co-glycolide)(PLG) microspheres, Journal of Microencapsulation, 2006, pp. 539-552, vol. 23, No. 5.
Boyer et al., Experimental Studies of Restricted Protein Diffusion in an Agarose Matrix, AIChE J., 1992, pp. 259-272, vol. 38, No. 2.
Chesko et al., An Investigation of the factors Controlling the Adsorption of Protein Antigens to Anionic PLG Microparticles, Pharm. Sci., 2005, pp. 2510-2519, vol. 94, No. 11.
Colman et al., Rapid Purification of Plasmid DNAs by Hydroxyapatite Chromatography, European Journal of Biochemistry, 1978, pp. 303-310, vol. 91.
Coombes et al., Biodegradable polymeric microparticles for drug delivery and vaccine formulation: the surface attachment of hydrophilic species using the concept of poly(ethylene glycol) anchoring segments, Biomaterials, 1997, pp. 1153-1161, vol. 18, No. 17.

(Continued)

*Primary Examiner* — Maury A Audet
(74) *Attorney, Agent, or Firm* — Sorell, Lenna & Schmidt, LLP

(57) ABSTRACT

Provided is a microsphere comprising a bead coated with a first calcium-containing mineral. Also provided is a method of producing a microsphere. Additionally, a method of administering a compound to a vertebrate is provided.

30 Claims, 14 Drawing Sheets
Specification includes a Sequence Listing.

(56) References Cited

OTHER PUBLICATIONS

Defail et al., Controlled release of bioactive doxorubicin from microspheres embedded within gelatin scaffolds, J. Biomed. Mater. Res. Part A, 2006, pp. 954-962, vol. 79A.

Driessens et al., Biological Calcium Phosphates and Their Role in the Physiology of Bone and Dental Tissues I. Composition and Solubility of Calcium Phosphates, Calcif. Tissue Res., 1978, pp. 127-137, vol. 26.

Ducheyne et al., Bioactive ceramics: the effect of surface reactivity on bone formation and bone cell function, Biomaterials, 1999, pp. 2287-2303, vol. 20.

Eniola et al., Characterization of biodegradable drug delivery vehicles with the adhesive properties of leukocytes, Biomaterials, 2002, pp. 2167-2177, vol. 23.

Extended European Search Report dated Jul. 2, 2014 in corresponding Application No. EP 09816920.4, 7 pages.

Fazan et al., Dissolution behavior of plasma-sprayed hydroxyapatite coatings, Journal of Materials Science: Materials in Medicine, 2000, pp. 787-792, vol. 11, No. 12.

Fernandez-Pradas et al., Deposition of hydroxyapatite thin films by excimer laser ablation, Thin Solid Films, 1998, pp. 393-396, vol. 317.

Ferreira et al., Human Embryoid Bodies Containing Nano- and Microparticulate Delivery Vehicles, Adv. Mater., 2008, pp. 2285-2291, vol. 20, and Supplementary Materials, 11 pages.

Fischer et al., One-step preparation of polyelectrolyte-coated PLGA microparticles and their functionalization with model ligands, Controlled Release 2006, pp. 135-144, vol. 111.

Gao et al., Bioinspired Ceramic Thin Film Processing: Present Status and Future Perspectives, Crystal Growth & Design, 2005, pp. 1983-2017, vol. 5, No. 5.

Gledhill et al., In vitro dissolution behaviour of two morphologically different thermally sprayed hydroxyapatite coatings, Biomaterials, 2001, pp. 695-700, vol. 22.

Green et al., Mineralized polysaccharide capsules as biomimetic microenvironments for cell, gene, and growth factor delivery in tissue engineering, Soft Matter, 2006, pp. 732-737, vol. 2.

Habibovic et al., Osteoinduction by biomaterials-Physicochemical and structural influences, Journal of Biomedical Materials Research Part A, 2006, pp. 747-762, vol. 77A, No. 4.

He et al., Nucleation of apatite crystals in vitro by self-assembled dentin matrix protein 1, Nature Materials, 2003, pp. 552-558, vol. 2, No. 8.

He et al., Spatially and Temporally Controlled Biomineralization is Facilitated by Interaction Between Self-Assembled Dentin Matrix Protein 1 and Calcium Phosphate Nuclei in Solution, Biochemistry, 2005, p. 16140-161485, vol. 44, No. 49.

Heinonen et al., A New and Convenient Colorimetric Determination of Inorganic Orthophosphate and Its Application to the Assay of Inorganic Pyrophosphatase, Analytical Biochemistry, 1981, pp. 313-317, vol. 113.

Hong et al., Hydroxyapatite/bacterial cellulose composites synthesized via a biomimetic route, Materials Letters, 2006, pp. 1710-1713, vol. 60, No. 13-14.

Hughes et al., Adsorption of bovine serum albumin onto hydroxyapatite, Biomaterials, 1995, pp. 697-702, vol. 16.

International Search Report and Written Opinion dated Dec. 24, 2009 in corresponding Application No. PCT/US09/58419 filed Sep. 25, 2009, 13 pages.

Jabbarzadeh et al., Apatite nano-crystalline surface modification of poly(lactide-co-glycolide) sintered microsphere scaffolds for bone tissue engineering: implications for protein adsorption, Journal of Biomaterials Science Polymer Edition, 2007, pp. 1141-1152, vol. 18, No. 9.

Jang et al., Controllable delivery of non-viral DNA from porous scaffolds, J. Controlled Release, 2003, pp. 157-168, vol. 86.

Japan Office Action dated Nov. 27, 2013 in corresponding Application No. 2011-529272, in Japanese, 2 pages.

Japan Office Action dated Nov. 27, 2013 in corresponding Application No. 2011-529272, English translation, 4 pages.

Jiang et al., Stabilization of a Model Formalinized Protein Antigen Encapsulated in Poly(lactide-co-glycolide)-Based Microspheres, J. Pharm. Sci., 2001, pp. 1558-1569, vol. 90, No. 10.

Jongpaiboonkit et al., Mineral-Coated Polymer Microspheres for Controlled Protein Binding and Release, Adv. Mater., 2009, pp. 1960-1963, vol. 21.

JP 2004-530675 published Oct. 7, 2004, abstract only in English, downloaded from espacenet.com, 2 pages.

Kawachi et al., Protein Adsorption Properties of Hydrothermally Prepared Hydroxyapatite, Key Eng. Mat., 2008, pp. 71-74, vols. 361-363.

Kokubo et al., Ca, P-rich layer formed on high-strength bioactive glass-ceramic A-W, Journal of Biomedical Materials Research, 1990, pp. 331-343, vol. 24, No. 3.

Kurumada et al., Formation of uniform hydroxyapatite nanocoating triggered by nucleation at carboxylic groups embedded in ethylene/acrylic acid copolymer microspheres, Colloids and Surfaces A: Physiochem. Eng. Aspects, 2008, pp. 34-39, vol. 322.

Legeros, Properties of Osteoconductive Biomaterials: Calcium Phosphates, Clin Ortho Rel Res., 2002, pp. 81-98, No. 395.

Leveque et al., Promotion of Fluorapatite Crystallization by Soluble-Matrix Proteins from Lingula Anatina Shells, Angewandte Chemie International Edition, 2004, pp. 885-888, vol. 43, No. 7.

Li et al., Apatite Formation Induced by Silica Gel in a Simulated Body Fluid, Journal of the American Ceramic Society, 1992, pp. 2094-2097, vol. 75, No. 8.

Lin et al., Surface reaction of stoichiometric and calcium-deficient hydroxyapatite in simulated body fluid, Journal of Materials Science-Materials in Medicine, 2001, pp. 731-741, vol. 12, No. 8.

Lu et al., Fabrication and Bioactivity of Porous Titanium Implant, Key Engineering Materials, 2007, pp. 613-616, vols. 342-343.

Luong et al., Spatial control of protein within biomimetically nucleated mineral, Biomaterials, 2006, pp. 1175-1186, vol. 27, No. 7.

Matsumoto et al., Hydroxyapatite particles as a controlled release carrier of protein, Biomaterials, 2004, pp. 3807-3812, vol. 25.

Meng et al., W/O/W double emulsion technique using ethyl acetate as organic solvent: effects of its diffusion rate on the characteristics of microparticles, J. Controlled Release, 2003, pp. 407-416, vol. 91.

Miyaji et al., Bonelike apatite coating on organic polymers, Novel nucleation process using sodium silicate solution, Biomaterials, 1999, pp. 913-919, vol. 20.

Moror et al., Solvent-induced collapse of a-synuclein and acid-denatured cytochrome c, Protein Sci., 2001, pp. 2195-2199, vol. 10.

Mu et al., Fabrication, characterization and in vitro release of paclitaxel (Taxol) loaded poly (lactic-co-glycolic acid) microspheres prepared by spray drying technique with lipid/cholesterol emulsifiers, J. Controlled Release, 2001, pp. 239-254, vol. 76.

Murphy et al., Growth of continuous bonelike mineral within porous poly(lactide-co-glycolide) scaffolds in vitro, Journal of biomedical Materials Research, 2000, pp. 50-58, vol. 50.

Murphy et al., Compartmental control of mineral formation: adaptation of a biomineralization strategy for biomedical use, Polyhedron, 2000, pp. 357-363, vol. 19.

Murphy et al., Bioinspired Growth of Crystalline Carbonate Apatite on Biodegradable Polymer Substrata, Journal of the American Chemical Society, 2002, pp. 1910-1917, vol. 124, No. 9.

Murphy et al., Synthesis and in Vitro Hydroxyapatite Binding of Peptides Conjugated to Calcium-Binding Moieties, Biomacromolecules, 2007, pp. 2237-2243, vol. 8.

Newman et al., Poly(D,L lactic-co-glycolic acid) microspheres as biodegradable microcarriers for pluripotent stem cells, Biomaterials, 2004, pp. 5763-5771, vol. 25.

O'Donnell et al., Preparation of microspheres by the solvent evaporation technique, Adv. Drug Deliver Rev., 1997, pp. 25-42, vol. 28.

Oyane et al., Preparation and assessment of revised simulated body fluids, Journal of Biomedical Materials Research Part A, 2003, pp. 188-195, vol. 65A.

Pandey et al., Nanoparticle-Based Oral Drug Delivery System for an Injectable Antibiotic -Streptomycin, Chemotherapy, 2007, pp. 437-441, vol. 53.

(56) References Cited

OTHER PUBLICATIONS

Pedraza et al., Osteopontin functions as an opsonin and facilitates phagocytosis by macrophages of hydroxyapatite-coated microspheres: Implications for bone wound healing, Bone, 2008, pp. 708-716, vol. 43, No. 4.

Pena et al., New method to obtain chitosan/apatite materials at room temperature, Solid State Sciences, 2006, pp. 513-519, vol. 8, No. 5.

Porjazoska et al., Poly(lactide-co-glycolide) microparticles as systems for controlled release of proteins—Preparation and characterization, Acta Pharm., 2004, pp. 215-229, vol. 54.

Qui et al., New bioactive, degradable composite microspheres as tissue engineering substrates, Journal of Biomedical Materials Research Part A, 2000, pp. 66-76, vol. 2, No. 1.

Raman et al., Modeling small-molecule release from PLG microspheres: effects of polymer degradation and nonuniform drug distribution, Journal of Controlled Release, 2005, pp. 149-158, vol. 103, No. 1.

Ruhe et al., Controlled release of rhBMP-2 loaded poly(DL-lactic-co-glycolic acid)/calcium phosphate cement composites in vivo, J. Controlled Release, 2005, pp. 162-171, vol. 106.

Schmaljohann, Thermo- and pH-responsive polymers in drug delivery, Adv. Drug Deliver Rev., 2006, pp. 1655-1670, vol. 58.

Schroder et al., Hydroxyapatite chromatography: altering the phosphate-dependent elution profile of protein as a function of pH, Analytical Biochemistry, 2003, pp. 176-178, vol. 313.

Su et al., Organization of apatite crystals in human woven bone, Bone, 2003, pp. 150-162, vol. 32.

Tanahashi et al., Apatite Coating on Organic Polymers by a Biomimetic Process, Journal of the American Ceramic Society, 1994, pp. 2805-2808, vol. 77, No. 11.

Uchida et al., Bonelike Apatite Formation Induced on Zirconia Gel in a Simulated Body Fluid and its Modified Solutions, Journal of the American Ceramic Society, 2001, pp. 2041-2044, vol. 84, No. 9.

Urist et al., Purification of bovine bone morphogenetic protein by hydroxyapatite chromatography, P. Natl. Acad. Sci. USA, 1984, pp. 371-375, vol. 81.

Vaupel et al., Blood Flow, Oxygen and Nutrient Supply, and Metabolic Microenvironment of Human Tumors: A Review, Cancer Res., 1989, pp. 6449-6465, vol. 49.

Wang et al., Preparation of hollow hydroxyapatite microspheres, J Mater Sci: Mater Med., 2006, pp. 641-646, vol. 17.

Yamaguchi et al., Enhancement of Albumin Expression in Bone Tissues With Healing Rat Fractures, J. Cell. Biochem., 2003, pp. 356-363, vol. 89.

Yamashita et al., Preparation of Apatite Thin Films through rf-Sputtering from Calcium Phosphate Glasses, Journal of the American Ceramic Society, 1994, pp. 2401-2407, vol. 77, No. 9.

Yang et al., Morphology, drug distribution, and in vitro release profiles of biodegradable polymeric microspheres containing protein fabricated by double-emulsion solvent extraction/evaporation method, Biomaterials, 2001, pp. 231-241, vol. 22.

Yokogawa et al., Growth of calcium phosphate on phosphorylated chitin fibres, Journal of Materials Science: Materials in Medicine, 1997, pp. 407-412, vol. 8.

Zhang et al., Biomimetic Polymer/Apatite Composite Scaffolds for Mineralized Tissue Engineering, Macromolecular Bioscience, 2004, pp. 100-111, vol. 4, No. 2.

D2—Xia, Lu, et al. "Fabrication and bioactivity of porous titanium implant," Key Engineering Materials, Trans Tech Publications, Switzerland. vol. 342, 2007, pp. 613-616.

D4—Pena, J., et al. "New method to obtain chitosan/apatite materials at room temperature," Solid State Sciences, Elsevier, Paris, France. vol. 8, No. 5, May 2006, pp. 513-519.

D5—Kurumada, K. I., et al: "Formation of uniform hydroxyapatite nanocoating triggered by nucleation at carboxylic groups embedded in ethylene/acrylic acid copolymer microspheres", Colloids and Surfaces. A, Physicachemical and Engineering Aspects, Elsevier, Amsterdam, NL, vol. 322, No. 1-3, Jun. 5, 2008 (Jun. 5, 2008), pp. 34-39.

D6—Pedraza, C. E., et al: "Osteopontin functions as an opsonin and facilitates phagocytosis by macrophages of hydroxyapatite-coated microspheres: Implications for bone wound healing", Bone, Pergamon Press., Oxford, GB.vol. 43, No. 4, Oct. 1, 2008 (Oct. 1, 2008), pp. 708-716.

D7—Qing, Wang, et al: "Preparation of hollow hydroxyapatite microspheres", Journal of Materials Science: Materials in Medicine, Kluwer Academic Publishers, BO, vol. 17, No. 7, Jul. 1, 2006 (Jul. 1, 2006), pp. 641-646.

European Search Report dated May 13, 2022 issued in corresponding European application No. 21213679.0.

* cited by examiner

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: modified peptide derived from osteocalcin

<400> SEQUENCE: 1

Ala Ala Ala Ala Glu Pro Arg Arg Glu Val Ala Glu Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: modified peptide derived from osteocalcin
<220> FEATURE:
<221> NAME/KEY: MISC_FEATURE
<222> LOCATION: (5)..(5)
<223> OTHER INFORMATION: carboxyglutamate
<220> FEATURE:
<221> NAME/KEY: MISC_FEATURE
<222> LOCATION: (9)..(9)
<223> OTHER INFORMATION: carboxyglutamate
<220> FEATURE:
<221> NAME/KEY: MISC_FEATURE
<222> LOCATION: (12)..(12)
<223> OTHER INFORMATION: carboxyglutamate

<400> SEQUENCE: 2

Ala Ala Ala Ala Xaa Pro Arg Arg Xaa Val Ala Xaa Leu
1               5                   10

<210> SEQ ID NO 3
<211> LENGTH: 7
<212> TYPE: PRT
```

```
<213> ORGANISM: Artificial Sequence
<220> FEATURE:
<223> OTHER INFORMATION: a cell adhesion peptide derived from
      fibronectin

<400> SEQUENCE: 3

Gly Gly Arg Gly Asp Ser Pro
1               5

<210> SEQ ID NO 4
<211> LENGTH: 7
<212> TYPE: PRT
<213> ORGANISM: Artificial Sequence
<220> FEATURE:
<223> OTHER INFORMATION: a cell adhesion peptide derived from laminin

<400> SEQUENCE: 4

Gly Gly Ile Lys Val Ala Val
1               5

<210> SEQ ID NO 5
<211> LENGTH: 7
<212> TYPE: PRT
<213> ORGANISM: Artificial Sequence
<220> FEATURE:
<223> OTHER INFORMATION: a cell adhesion peptide derived from laminin

<400> SEQUENCE: 5

Gly Gly Tyr Ile Gly Ser Arg
1               5

<210> SEQ ID NO 6
<211> LENGTH: 6
<212> TYPE: PRT
<213> ORGANISM: Artificial Sequence
<220> FEATURE:
<223> OTHER INFORMATION: a cell adhesion/signaling peptide derived from
      type I collagen

<400> SEQUENCE: 6

Gly Gly Asp Gly Glu Ala
1               5

<210> SEQ ID NO 7
<211> LENGTH: 22
<212> TYPE: PRT
<213> ORGANISM: Artificial Sequence
<220> FEATURE:
<223> OTHER INFORMATION: a peptide derived from bone morphogenetic
      protein-2

<400> SEQUENCE: 7

Gly Gly Lys Ile Pro Lys Ala Ser Ser Val Pro Thr Glu Leu Ser Ala
1               5                   10                  15

Ile Ser Thr Leu Tyr Leu
            20
```

MINERAL-COATED MICROSPHERES

CROSS-REFERENCE TO RELATED APPLICATIONS

This application claims the benefit of U.S. Provisional Application No. 61/100,062, filed Sep. 25, 2008 and is incorporated herein by reference in its entirety.

STATEMENT REGARDING FEDERALLY SPONSORED RESEARCH OR DEVELOPMENT

This invention was made with government support under grant R03AR052893 awarded by The National Institutes of Health. The government has certain rights in the invention.

BACKGROUND

The present application generally relates to tissue engineering and administration of therapeutic compounds.

Biodegradable microspheres have been widely used as carriers for controlled release of drug molecules, including small molecules (DeFail et al. 2006), DNA (Jang and Shea, 2003), and proteins (Yang et al. 2001). Although these carriers have become prevalent in biomedical applications ranging from injectable drug delivery (Pandy and Khuller, 2007) to manipulation of stem cell differentiation (Newman and McBurney, 2004; Ferreira et al. 2008), protein release from these microspheres is often confounded by low molecule encapsulation efficiency (Akhtar and Lewis, 1997), "burst" release of molecules over short timescales (O'Donnell and Mcginity, 1997), and decreased activity of biological molecules due to microsphere processing conditions and polymer degradation by products (Jiang and Schwendeman, 2001).

Hybrid materials composed of organic polymers coated with inorganic minerals have attracted much attention in biology and medicine due to their combination of advantageous properties. Polymeric materials are a desirable base material for biomedical applications, as they can be processed into a variety of sizes and geometries, and can be designed to bioresorb in a controllable timeframe. Therefore, polymeric biomaterials have been featured in a variety of applications, including medical devices, tissue engineering scaffolds, and drug delivery systems.

Calcium phosphate based mineral coatings represent desirable surfaces for biomedical applications, as they are similar in composition to bone tissue, and have been shown to promote favorable interactions with natural bone, a property termed "bioactivity". For example, hydroxyapatite—the major inorganic component of bone mineral—is osteoconductive (Ducheyne et al., 1999), and may also be capable of inducing new bone formation in vivo (Habibovic et al., 2006).

A particular subset of approaches used to grow hydroxyapatite coatings on biomaterials surfaces mimics some aspects of natural biomineralization processes, and has therefore be termed "biomimetic" or "bioinspired" Hong et al., 2006; Gao and Koumoto, 2005; Leveque et al., 2004; Green et al., 2006). This type of approach is a practically and economically attractive alternative to high-temperature commercial processing methods such as plasma-spraying (Gledhill et al., 2001), sputter coating (Yamashita et al., 1994), and laser deposition (Fernandez-Pradas et al., 1998). Kokubo et al. first reported bioinspired growth of apatite coatings on bioactive CaO—$SiO_2$ glass in a simulated body fluid (SBF), which had ion concentrations nearly equal to those of human blood plasma and was held at physiologic temperature and pH (Kokubo et al., 1990). A series of subsequent studies reported mineral growth using novel formulations of SBF (Oyane et al., 2003), variation in the mineral growth process (Miyaji et al., 1999), or variations in the base materials (Yogogawa et al., 1997). The basis for mineral nucleation in these studies involved interactions of mineral ions in solution with polar functional groups on the materials surface, such as Si—OH (Li et al., 1992), Ti—OH (Barrere et al., 2004) and Zr—OH (Uchida et al., 2001). A series of recent studies has extended the bioinspired mineralization process to include formation of a bone-like hydroxyapatite coating on biodegradable polymer films (Murphy and Mooney, 2002) or porous scaffolds (Murphy et al., 2000; Zhang and Ma, 2004; Bajpai and Singh, 2007). The mechanism for mineral nucleation and growth on these materials is based on the interaction of carboxylate and hydroxyl groups on the hydrolyzed surface with calcium- and phosphate-rich nuclei in solution, creating a driving force for heterogeneous nucleation and mineral growth (Murphy and Mooney, 2002). This coating process is particularly suitable for biodegradable polymers, as it can be carried out at physiological temperature and pH (Tanahashi et al., 1994), and the mild processing conditions also suggest that it is possible to incorporate biologically active molecules such as polypeptides and polynucleotides, during the coating process.

There is a need for new applications of mineral-coated polymers for use in therapeutic treatments. Those needs are addressed herein.

SUMMARY

The inventors have discovered that microspheres can be produced that have a calcium-containing mineral coating. See Examples. These microspheres are useful, at least for providing slow release of therapeutic compounds combined therewith.

The application is directed to a microsphere comprising a bead coated with a first calcium-containing mineral.

The application is also directed to a method of producing a microsphere. The method comprises incubating a bead in a physiological saline solution comprising carbonate, calcium, and phosphate such that a first calcium-containing mineral layer coating forms on the bead. In this method, the bead with the mineral layer coating is the microsphere.

In other embodiments, the application is directed to a method of administering a compound to a vertebrate. The method comprises administering the above microsphere to the vertebrate.

BRIEF DESCRIPTION OF THE DRAWINGS

FIG. 1 is a schematic and micrographs of PLG microspheres before and after mineral coating.

FIG. 2 are graphs of XRD and FTIR spectra. Panel A shows a representative XRD spectrum of mineral-coated microspheres showing apatite peaks corresponding to hydroxyapatite at 2θ=25.78°, 28.68°, and 32.05°. Panel B shows a representative FTIR spectrum showing phosphate peaks (1087, 1035, 950, 560 $cm^{-1}$) and carbonate peaks (1456 and 1415 $cm^{-1}$).

FIG. 3 is graphs and a micrograph relating to protein binding on mineral-coated microspheres. Panel A is a representative FT-IR spectrum of protein bound onto mineral-coated microspheres showing phosphate peaks (1087, 1035, 950, 560 $cm^{-1}$), carbonate peaks (1456 and 1417 $cm^{-1}$), and amide peaks (1653 and 1558 cm$^{-1}$). Panel B is a scanning electron micrograph (SEM) of protein bound on the surface of mineral, scale bar=100 nm. Panel C shows binding curves of bovine serum albumin (BSA) and Cytochrome c (Cyt c) on the mineral-coated microspheres surface.

FIG. 4 is graphs and micrographs relating to release of protein from mineral-coated microspheres. Panel A is a comparison of cumulative release of BSA bound to mineral-coated PLG microspheres and BSA encapsulated in PLG microspheres. Both approaches show sustained release, with the total amount of bound BSA release significantly higher than the encapsulated BSA after 30 days. Panels B and C are SEM images of mineral-coated microspheres (B); and PLG microspheres (C) after the 30 day release period. Panel D shows cumulative release of Cyt c from mineral-coated PLG microspheres at pH 4 and pH 7.4. Panels E and F are SEM images of mineral-coated microspheres after 30 days of release in buffered solutions pH=4 (E), and pH=7.4 (F).

FIG. 5 is SEM images of a PLG microsphere (A) and mineral-coated microsphere after incubation in mSBF for 7 days.

FIG. 6, Panels A-D are SEM images of mineral-coated microspheres after a 7 day incubation in mSBF solution, 0.25% w/v (A), 0.50% w/v (B), 0.75% w/v (C), and 1.00% (D) w/v. Panel E is a graph showing the relationship between the microsphere concentration in solution during mineral growth, and the size of mineral-coated microsphere aggregates.

Figure 10:
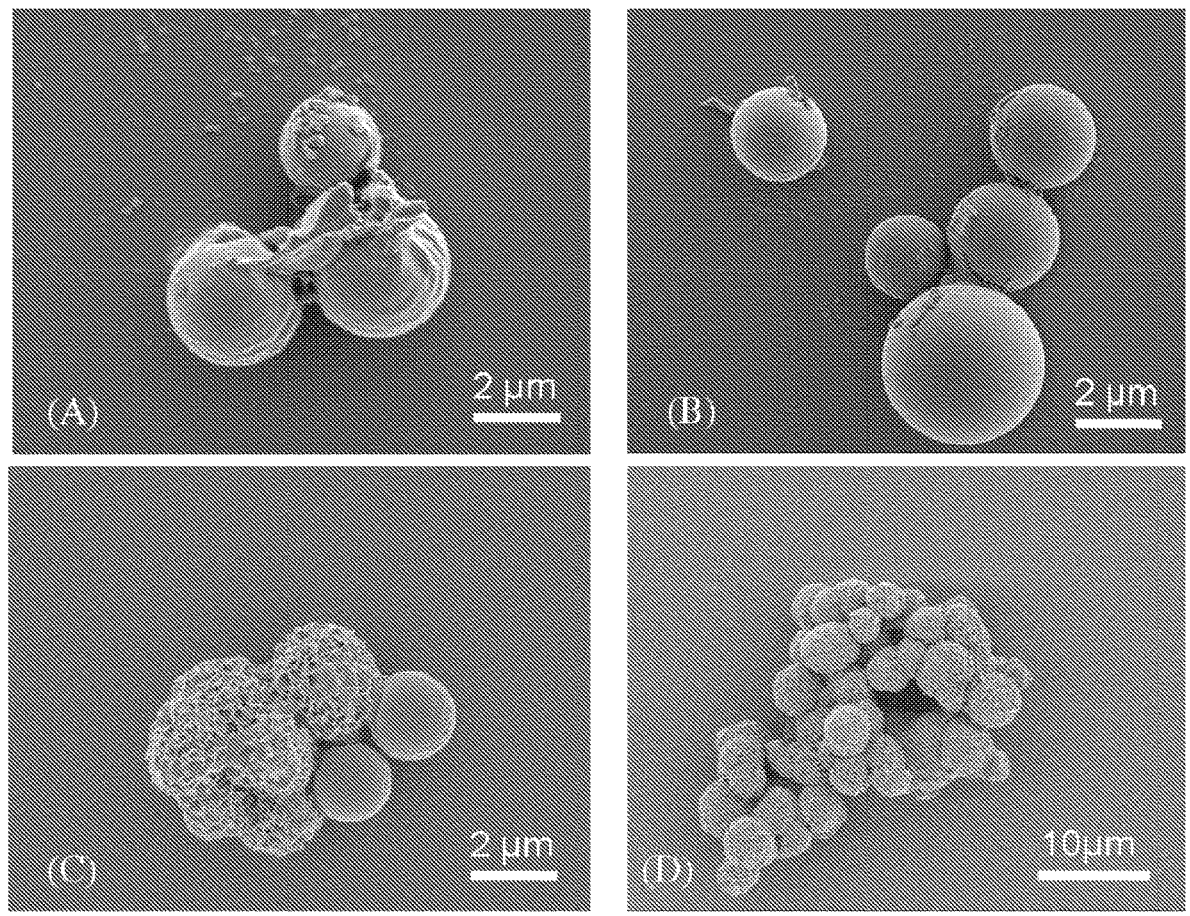

FIG. 10 is SEM images showing the process of mineral nucleation and growth on PLG microspheres. The images are of microspheres after: the first day of immersion in mSBF (A), day 3 of incubation (B), day 5 of incubation (C) and day 7 of incubation (D).

Figure 11:
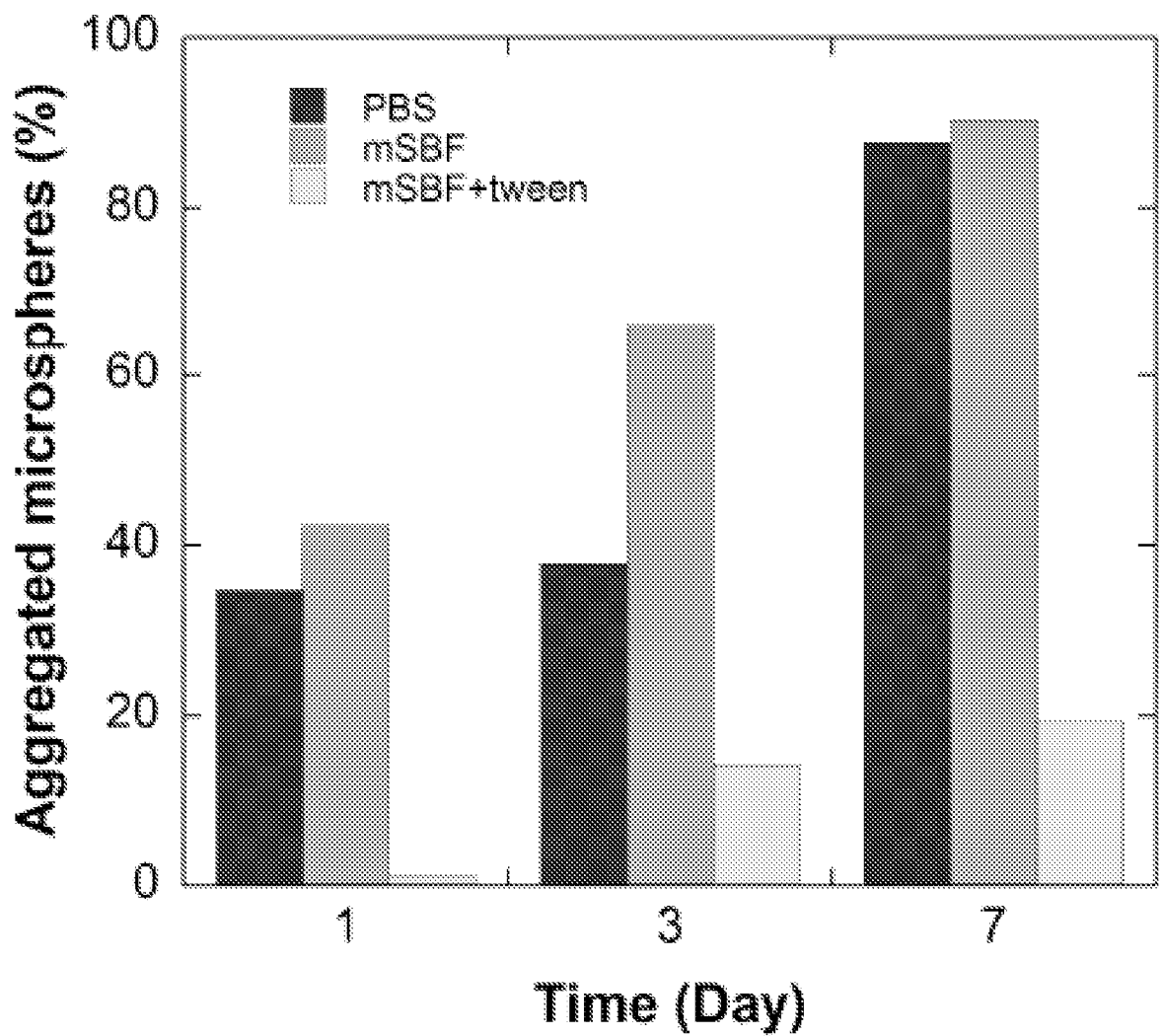

FIG. 11 is a graph showing the percentage of aggregated microspheres suspended for 1, 3 and 7 days in PBS, mSBF and mSBF+Tween20™.

Figure 12:
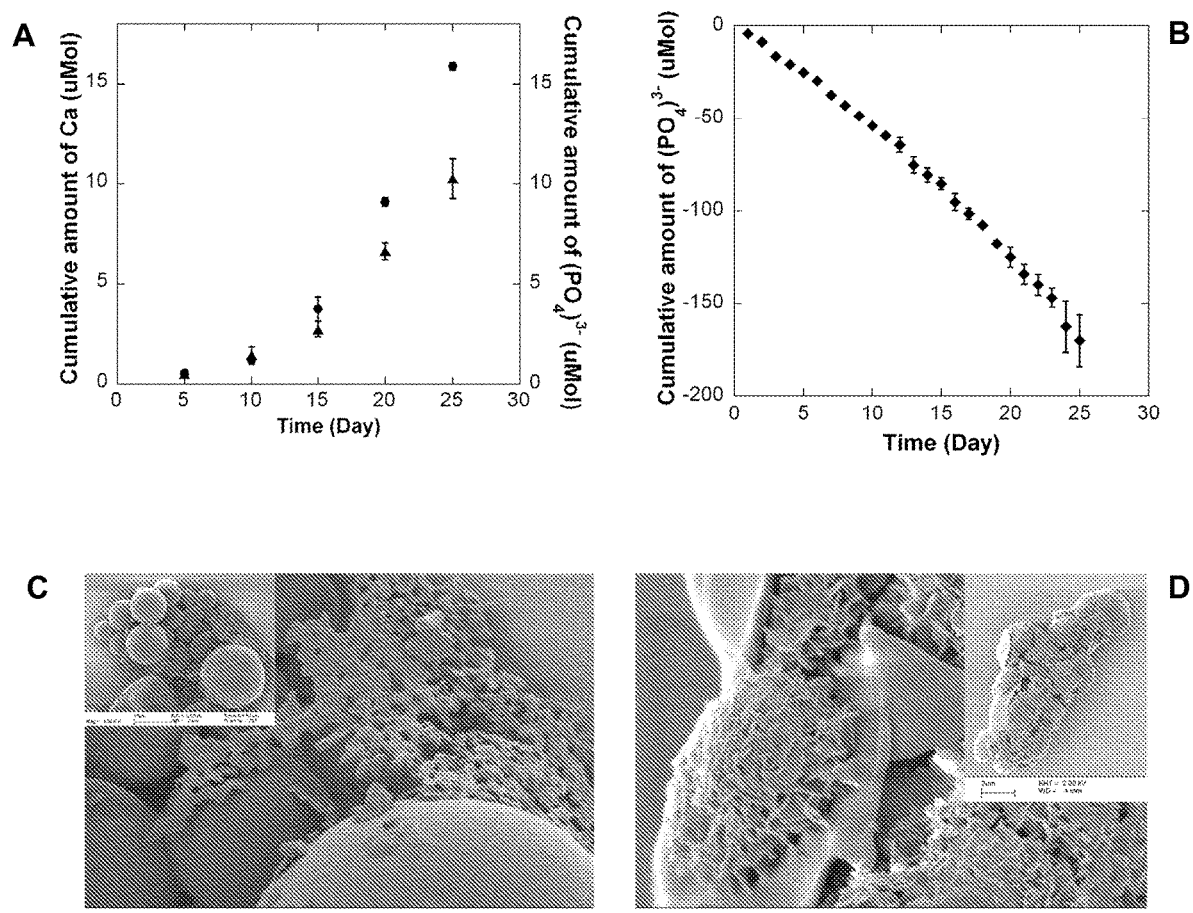

FIG. 12 is graphs and SEM images of mineral dissolution of mineral-coated microspheres. Panel A shows cumulative dissolution of $Ca^{2+}$ and $PO_4^{3-}$ during a 25 day incubation in tris-buffered saline (TBS). Panel B shows cumulative dissolution of $PO_4^{3-}$ during a 25 day incubation in DMEM. Panels C is SEM images of mineral-coated microspheres after the 25 day TBS incubation. Panel D is SEM images of mineral-coated microspheres after the 25 day DMEM incubation.

Figure 13:
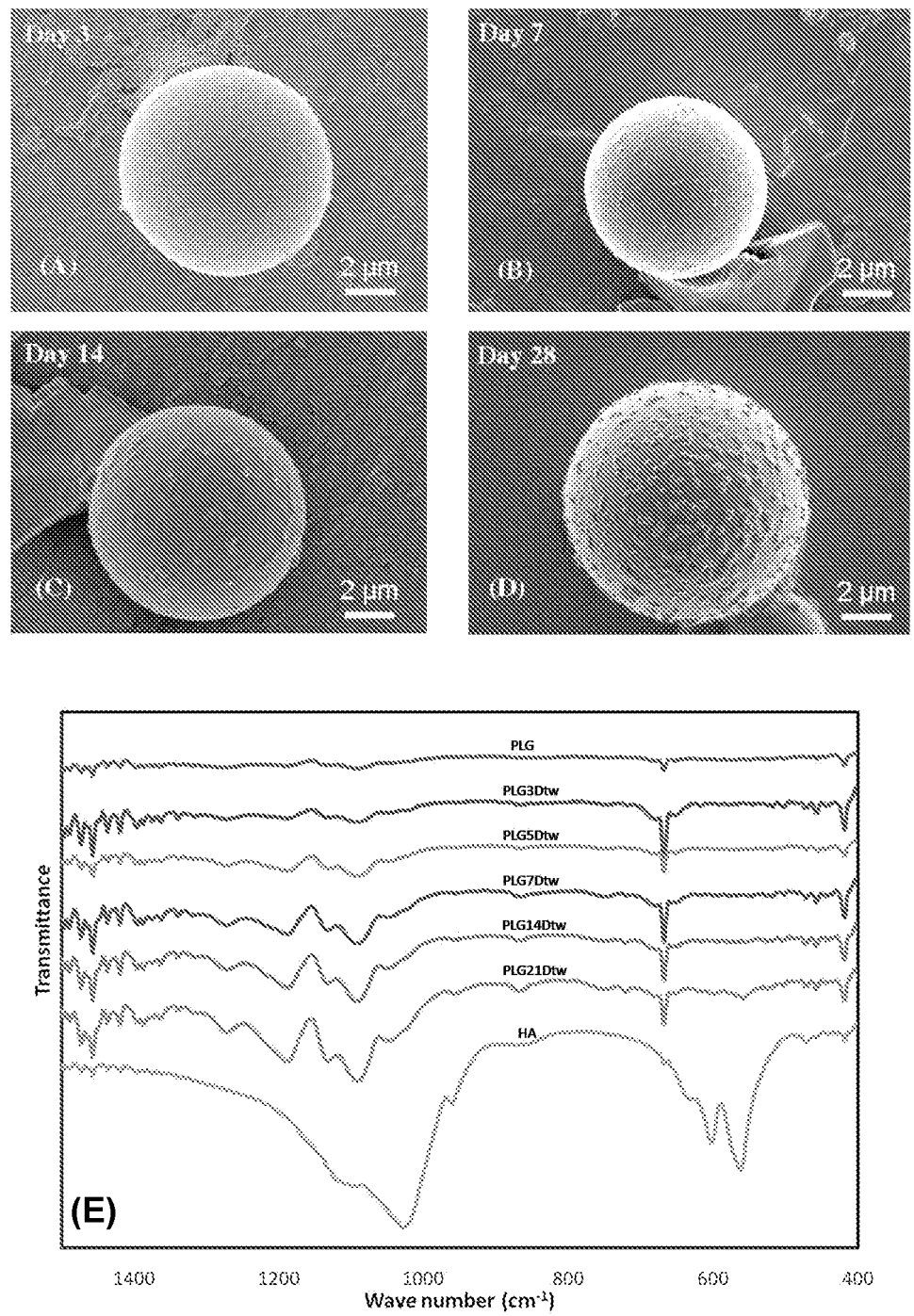

FIG. 13 is SEM images and a graph showing the effect of surfactant (Tween 20™) on the mineral formed on the PLG microsphere surfaces after 3 days (A), after 7 days (B), after 14 days (C), and after 28 days (D). Panel E shows an FTIR spectrum of PLG microspheres coated with mineral via a 28 day mSBF incubation in the presence of 0.1% v/v Tween 20™. A spectrum of commercial HA powder is included for comparison.

Figure 14:
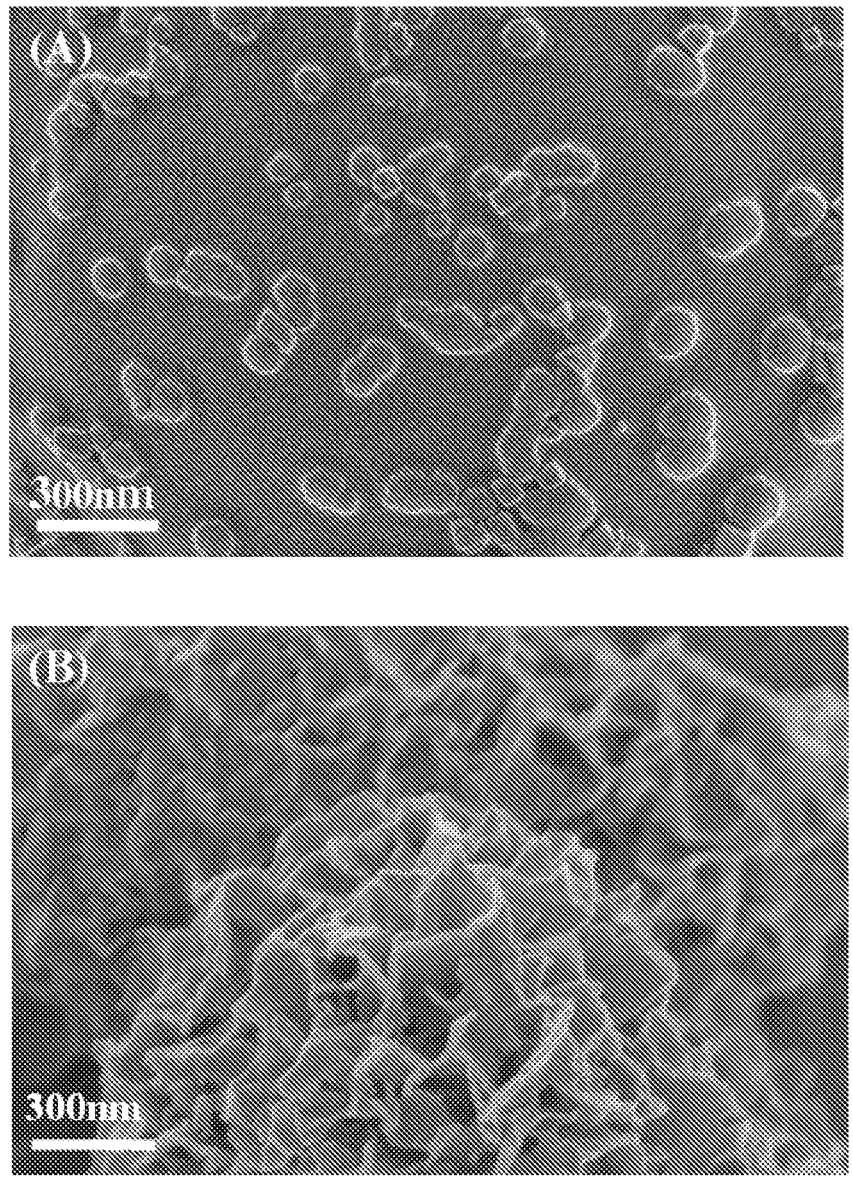

FIG. 14 is SEM images showing nanometer-scale mineral morphology on the surface of microspheres formed in the presence (A) or absence (B) of 0.1% v/v Tween 20™.

DETAILED DESCRIPTION

The inventors have developed methods for producing novel microspheres that have a calcium-containing mineral coating. They have also characterized these microspheres and established that they have advantageous properties useful for utilizing the microspheres to deliver therapeutic compounds to tissues. See Examples.

In some embodiments, the application is directed to a microsphere comprising a bead coated with a first calcium-containing mineral. The Examples describe exemplary methods for producing these microspheres using a modified simulated body fluid (mSBF). By adjusting the mineral composition, and/or concentration of the mSBF, the composition of the mineral precipitated on the microspheres can be manipulated. See also U.S. Patent Application Publication US 2008/0095817 A1; U.S. Pat. No. 6,767,928 B1; U.S. Pat. No. 6,541,022 B1; PCT Publication WO 2008/070355 A2; PCT Publication WO 2008/082766 A2; Murphy and Mooney, 2001; Murphy and Messersmith, 2000.

Inorganic minerals suitable for producing a calcium-containing mineral coating include various bone mineral ions, such as, but not limited to calcium and phosphate and combinations of bone mineral ions, such as calcium-phosphates. The calcium-containing mineral coating can comprise, e.g., hydroxyapatite (HAP), α-tricalcium phosphate (α-TCP), β-tricalcium phosphate (β-TCP), amorphous calcium phosphate, dicalcium phosphate, octacalcium phosphate or calcium carbonate. The calcium-containing mineral coating can comprise a plurality of layers, e.g., separate layers having distinct dissolution profiles. Under physiological conditions, solubility of calcium phosphate species adhere to the following trend: amorphous calcium phosphate>dicalcium phosphate>octacalcium phosphate>β-TCP>HAP. A dicalcium phosphate mineral will typically have a dissolution rate that is more than fifty times higher than that of HAP. Therefore, creation of a matrix with distinct calcium phosphate layers allows for a broad range of dissolution patterns.

The bead can be formed of any suitable material known in the art. The selection of the bead material for any particular application can be made without undue experimentation.

In some embodiments, the bead comprises a negative charge, which can promote the deposition of the calcium containing material. The negative charge could be provided by any moiety present on the bead, for example a carboxylate group, as is present in poly(D,L-lactide-co-glycolide) (PLG). In some embodiments the bead is made of a polymer, for example a synthetic polymer. In various aspects of these embodiments, the polymer is bioabsorbable. Nonlimiting examples of suitable bead materials include, for example, a collagen gel, polyvinyl alcohol, a marine adhesive protein, a PLG fiber matrix, a polyglactin fiber, a calcium alginate gel, a polyglycolic acid, polyester (e.g., poly-(L-lactic acid) or a polyanhydride), a polysaccharide (e.g. alginate), chitosan, polyphosphazene, polyacrylate, polyethylene oxide-polypropylene glycol block copolymer, fibrin, collagen, and fibronectin, polyvinylpyrrolidone, hyaluronic acid, poly(lactide), poly(glycolic acid), poly(lactide-co-glycolide), poly (caprolactone), polycarbonates, polyamides, polyanhydrides, polyamino acids, polyortho esters, polyacetals, polycyanoacrylates), polyurethanes, polyacrylates, ethylene-vinyl acetate polymers and other acyl substituted cellulose acetates and derivatives thereof), polyurethanes, polystyrenes, polyvinyl chloride, polyvinyl fluoride, poly (vinylimidazole), chlorosulphonated polyolifins, polyethylene oxide, polyvinyl alcohol, Teflon®, nylon, and analogs, mixtures, combinations and derivatives of any of the above.

In various embodiments, the bead is made of a polymer that comprises polar oxygen groups. Examples of such polymers include polycarboxylates, polyanhydrides, poly (α-hydroxyesters), poly(ethylene terephthalates), poly(carbonates), poly(amides), poly(lactones), a poly(saccharides) and poly(acrylates).

In various embodiments, the bead is made of a PLG, for example at a ratio of about 85:15 lactide:glycolide ("85:15 PLG"). The use of 85:15 PLG copolymers is advantageous as a decrease in the lactide/glycolide ratio of the copolymer is believed to increase the rate of surface hydrolysis.

In certain specific embodiments, the first calcium-containing mineral is a carbonated-substituted calcium-deficient hydroxyapatite and the bead is PLG, wherein the PLG is about 85:15 lactide:glycolide.

In some embodiments, the microsphere further comprises a component adhering to the first calcium-containing mineral, wherein the component introduces a functional group to the first calcium-containing mineral. Introduction of such a functional group allows covalent binding of any additional materials (e.g. therapeutic compounds) to the microspheres. Nonlimiting examples of functional groups that can be introduced on the component is a carboxylate, an amine, a carbonyl, a nitro, a hydroxyl, an aldehyde, or an ester. In some embodiments, the component comprises a poly(aspartic acid), a poly(glutamic acid), or a bisphosphonate. See e.g., Murphy et al., 2007. Other nonlimiting examples of components useful in these embodiments are the oligopeptides AAAAEPRREVAEL or AAAAγEPRRγEVAγEL, where γE is carboxyglutamate.

In some embodiments, the microsphere further comprises a first compound adhering to the first calcium-containing mineral or the component.

In certain specific embodiments of the first compound-containing microspheres, the first calcium-containing mineral is a carbonated-substituted calcium-deficient hydroxyapatite and the bead is poly(D,L-lactide-co-glycolide) (PLG), wherein the PLG is about 85:15 lactide:glycolide.

These embodiments are not limited to any particular first compounds. The first compound can be an organic compound less than 2000 MW, or less than 1000 MW, or less than 500 MW. Nonlimiting examples include antibiotics, corticosteroids and statins. More specific examples include cefazolin, cefuroxime, clindamycin, vancomycin and dexamethasone.

Alternatively, the first compound can be an oligopeptide or polypeptide. As used herein, an oligopeptide comprises a linear chain of 30 or less amino acids. A polypeptide comprises more than 30 amino acids. Examples of oligopeptides are GGRGDSP (a cell adhesion peptide derived from fibronectin), GGIKVAV (a cell adhesion peptide derived from laminin), GGYIGSR (a cell adhesion peptide derived from laminin), GGDGEA (a cell adhesion/signaling peptide derived from type I collagen), GGKIPKASSVPTELSAISTLYL (a peptide derived from bone morphogenetic protein-2), AAAAEPRREVAEL (a modified peptide derived from osteocalcin—some affinity for hydroxyapatite mineral), AAAAγEPRRγEVAγEL, where γE is carboxyglutamate (a modified peptide derived from osteocalcin—high affinity for hydroxyapatite mineral).

In other embodiments, the first compound is a polypeptide, for example a cytokine, an enzyme, or a protein comprising an antibody binding site (e.g., an antibody). Other nonlimiting examples of polypeptides that could be included in the microspheres are virtually any hormone, neurotransmitter, growth factor, growth factor receptor, interferon, interleukin, chemokine, cytokine, colony stimulating factor and/or chemotactic factor protein or polypeptide. Further examples include transcription or elongation factors, cell cycle control proteins, kinases, phosphatases, DNA repair proteins, oncogenes, tumor suppressors, angiogenic proteins, anti-angiogenic proteins, immune response stimulating proteins, cell surface receptors, accessory signaling molecules, transport proteins, enzymes, anti-bacterial and/or anti-viral proteins or polypeptides, and the like, depending on the intended use of the ultimate composition. More specific examples include growth hormone (GH); parathyroid hormone (PTH, including PTH1-34); bone morphogenetic proteins (BMPs), such as BMP-2A, BMP-2B, BMP-3, BMP-4, BMP-5, BMP-6, BMP-7 and BMP-8; transforming growth factor-α (TGF-α), TGF-β1 and TGF-β2; fibroblast growth factor (FGF); granulocyte/macrophage colony stimulating factor (GMCSF); epidermal growth factor (EGF); platelet derived growth factor (PDGF); an insulin-like growth factor (IGF), leukemia inhibitory factor (LIF), vascular endothelial growth factor (VEGF), basic fibroblast growth factor (bFGF), platelet derived growth factor (PDGF), angiogenin, angiopoietin-1, del-1, follistatin, granulocyte colony-stimulating factor (G-CSF), hepatocyte growth factor/scatter factor (HGF/SF), interleukin-8 (IL-8), leptin, midkine, placental growth factor, platelet-derived endothelial cell growth factor (PD-ECGF), platelet-derived growth factor-BB (PDGF-BB), pleiotrophin (PTN), progranulin, proliferin, tumor necrosis factor-α (TNF-α), a matrix metalloproteinase (MMP), angiopoietin 1 (ang1), ang2, and delta-like ligand 4 (DLL4).

In some specific embodiments, the polypeptide is a BMP-2, a BMP-7, a VEGF, an FGF-2, a PDGF, a TGF-β, an interleukin, or a human GH.

The first compound can also be a nucleic acid. Nonlimiting examples include a microRNA, an antisense nucleic acid, and a vector. Where the first compound is a vector, any vector known or later discovered can be included here. In some embodiments, the vector comprises a sequence encoding a therapeutic protein, such as any of the proteins discussed above.

The first compound can noncovalently adhere to the microsphere. Alternatively, the microsphere can further comprise a component adhering to the first calcium-containing mineral and introducing a functional group to the microsphere, to which the compound is covalently attached. See, e.g., Murphy et al., 2007.

In some embodiments, the first compound is at more than one level of the first calcium-containing mineral. These microspheres generally release the compound over a longer period of time than where the compound is only at one level (for example the outer surface of the first calcium-containing mineral.

In other embodiments, the first compound is modified to change the rate at which the compound is released from the microsphere. For example, where the first compound further comprises a moiety that increases the strength of binding of the compound to the first calcium-containing mineral, the compound would be released more slowly than if the moiety is not present. Nonlimiting examples of such moieties include amino acid sequences rich in glutamic acid, aspartic acid or phosphoserine, which interact directly with calcium ions in mineralized extracellular matrices. Other examples include AAAAEPRREVAEL or AAAAγEPRRγEVAγEL, where γE is carboxyglutamate.

In various embodiments, the microsphere further comprises a second compound adhering to the first calcium-containing mineral or the component. As with the first compound, the microspheres are not limited as to the nature of the second compound. The second compound can be for example an organic compound less than 2000 MW or 1000 MW or 500 MW. Alternatively, the second compound can be an oligopeptide or polypeptide, or a nucleic acid. In these embodiments, the first compound and the second compound can be on the same or different levels of the first calcium-containing minerals. Having the two compounds on different levels is useful when it is desired that the two compounds are released at different times. The microsphere can also further comprise a third, fourth, fifth, etc. compound as desired.

In additional embodiments, the microsphere comprises a living cell. The living cell can be from any organism, including an Archaea, a prokaryote, or a eukaryote. In some embodiments, the cell is a mammalian cell. The cell can be naturally occurring or, alternatively, can be transformed to express a recombinant molecule, e.g., a protein or nucleic acid (such as an miRNA).

In certain specific embodiments of these cell-containing microspheres, the first calcium-containing mineral is a carbonated-substituted calcium-deficient hydroxyapatite and the bead is poly(D,L-lactide-co-glycolide) (PLG), wherein the PLG is about 85:15 lactide:glycolide.

The cell can be adhered to the microsphere by any known means. In some embodiments, the microsphere comprises a first binding agent that binds to a second binding agent on the cell. Nonlimiting examples of such agents are a receptor and a ligand of the receptor, complementary nucleic acids, or a cell adhesion peptide and a ligand of the cell adhesion peptide. In the latter case, examples of suitable cell adhesion peptides are GGRGDSP, GGIKVAV, GGYIGSR or GGDGEA. These peptides or any other first binding agent can be part of a larger molecule, for example a molecule that binds to the first calcium-containing mineral as discussed above.

In some embodiments, the microsphere comprises a cell as well as a compound (e.g., a cytokine) that interacts with the cell. In such a microsphere, the cytokine is advantageously close to the cell, such that the compound is likely to contact and thus interact with the cell.

In additional embodiments, the microsphere further comprises a coating of a second calcium-containing mineral. The second coating can be a mineral that has a different degradation rate than the first calcium-containing mineral. The microsphere comprising the two coatings can further comprise one or more than one compound. Either of the two coatings can be, for example, any of hydroxyapatite (HAP), α-tricalcium phosphate (α-TCP), β-tricalcium phosphate (β-TCP), amorphous calcium phosphate, dicalcium phosphate, octacalcium phosphate or calcium carbonate. For example, the first calcium-containing mineral can be hydroxyapatite and further comprises a first therapeutic compound, and the second calcium-containing mineral can be α-TCP and is coated above (i.e., closer to the surface of the microsphere) the first calcium containing mineral and further comprises a second therapeutic compound. In this example, the second calcium-containing mineral would degrade first, releasing the second therapeutic compound before the first therapeutic compound is released.

Where a compound is present in the microsphere, its release depends on a number of factors, for example (a) how strongly the compound adheres to the calcium-containing mineral or component, (b) how far away from the surface of the microsphere the compound is (for example if a layer of calcium-containing mineral is deposited on the microsphere after the compound is added), (c) the degradation/bioabsorption rate of the calcium-containing mineral, (d) whether the compound is covalently bound to a component, and if so, (e) how strongly the component is bound to the mineral, (f) how strongly the covalent bond is between the compound and the component, and (g) whether there are enzymes present, e.g., from a tissue in which the microsphere is implanted, that will break the covalent bond and release the compound. Each of these factors may have more or less influence on the release of the compound, depending on the configuration of the microsphere. For example, in the case where the compound is covalently attached to a component, the component binds to the calcium-containing material strongly, and there are no enzymes to break the covalent bond, then the main factor influencing the release of the component is the rate of degradation of the calcium-containing mineral. However, if the compound is noncovalently adhering directly to the calcium-containing mineral, then all of the above factors (a)-(c) will have an influence in the rate of release of the compound.

In further embodiments, the compound is in the bead. In these embodiments, the compound would likely be released upon degradation of the bead, after the degradation of the calcium-containing mineral.

In some embodiments, the various microspheres discussed herein generally have a diameter between about 0.5 μm and about 500 μm. In other embodiments, the microsphere has a diameter between about 0.5 μm and about 100 μm. In additional embodiments, the microsphere has a diameter between about 2 μm and about 6 μm.

As discussed in the examples the microspheres tend to aggregate, particularly if they are produced by incubation in mSBF at a high concentration of microspheres or for an extended period of time (see Examples). Thus, in some embodiments, the application is directed to a plurality of any of the above-described microspheres, aggregated. In certain specific embodiments of these aggregated microspheres, the first calcium-containing mineral is a carbonated-substituted calcium-deficient hydroxyapatite and the bead is poly(D,L-lactide-co-glycolide) (PLG), wherein the PLG is about 85:15 lactide:glycolide. In other embodiments of these aggregated microspheres, a first compound, as described above, adheres to the first calcium-containing mineral.

The application is also directed to a method of producing a microsphere. The method comprises incubating a bead in a physiological saline solution comprising carbonate, calcium, and phosphate such that a first calcium-containing mineral layer coating forms on the bead, where the bead with the mineral layer coating is the microsphere. See Examples. In some embodiments, the solution comprises NaCl, KCl, $MgCl_2$, $MgSO_4$, $NaHCO_3$, Tris, $CaCl_2$, and $KH_2PO_4$. In more specific embodiments, the solution comprises about 100-200 mM NaCl, about 1-8 mM KCl, about 0.1-2 mM $MgSO_4$, about 0.2-5 mM $MgCl_2$, about 1-100 mM $NaHCO_3$, about 2-20 mM $CaCl_2$, and about 0.5-10 mM $KH_2PO_4$. Even more specifically, the solution comprises about 141 mM NaCl, about 4.0 mM KCl, about 0.5 mM $MgSO_4$, about 1.0 mM $MgCl_2$, about 4.2 mM $NaHCO_3$, about 5.0 mM $CaCl_2$, and about 2.0 mM $KH_2PO_4$.

In some of these methods, the solution also comprises a surfactant, which can change the morphology of the calcium-containing mineral layer, and reduce aggregation of the microspheres. See Example 2. Any surfactant now known or later discovered may be used here. In some embodiments, the surfactant is Tween 20™.

In some embodiments, the mineral coating described herein is developed by incubating the constituents in the above solution, which can be called a "simulated body fluid" (SBF) or a "modified simulated body fluid" (mSBF), for five days or more at a pH of about 6.8 to about 7.4 and at a temperature of about 37° C. The SBF or mSBF may be refreshed daily. Using the chemical composition described in the Examples, the procedure produces a calcium-deficient, carbonate-containing apatite material on alginate and on poly-(α-hydroxy esters). See U.S. Pat. No. 6,767,928, incorporated herein by reference. mSBF includes elevated calcium and phosphate. In general, an increase in pH favors hydroxyapatite growth, while a decrease in pH favors octacalcium phosphate mineral growth.

For example, conditions favorable for hydroxyapatite formation include a pH between about 5.0 and about 8.0 and a calcium concentration multiplied by a phosphate concentration between about $10^{-5}$ and about $10^{-8}$ M. Likewise, conditions favorable for octacalcium phosphate formation include a pH between about 6.0 and about 8.0 and a calcium concentration multiplied by a phosphate concentration between about $10^{-5}$ and about $10^{-7.5}$ M. Furthermore, conditions favorable for dicalcium phosphate dehydrate formation include a pH between about 6.0 and about 8.0 and a calcium concentration multiplied by a phosphate concentration between about $10^{-4}$ and about $10^{-6}$ M.

Specifically, using poly-(α-hydroxy esters) or alginate hydrogels as a template, one would vary the pH of mSBF between about 5.0 and about 6.0 to promote hydroxyapatite formation. Similarly, one would vary the pH of mSBF between about 6.0 and about 6.5 to promote octacalcium phosphate and hydroxyapatite formation. Likewise, one would vary the pH of mSBF between about 6.5 and about 8.0 to promote dicalcium phosphate, octacalcium phosphate and hydroxyapatite formation.

Prior to deposition of the first calcium-containing mineral, the bead may be surface-functionalized to allow increased mineral deposition by utilizing chemical pre-treatment to achieve surface hydrolysis, e.g., using an NaOH solution. Surface degradation by this technique causes an increase in the amount of polar oxygen functional groups on the surface of the material. The functionalized surface is then incubated in a mineral-containing solution.

In some embodiments, the method further comprises adding a component that adheres to the first calcium-containing mineral layer to the microsphere. In these embodiments, the component introduces a functional group to the first calcium-containing mineral layer. As discussed previously, nonlimiting examples of such components include peptides comprising a poly(aspartic acid) sequence, a poly(glutamic acid) sequence, AAAAEPRREVAEL and AAAAγEPRRγEVAγEL, where γE is carboxyglutamate.

In additional embodiments, the method further comprises incubating the microsphere with a first compound such that the first compound adheres to the microsphere. As discussed above in relation to the discussion on the microsphere composition, the first compound can be any chemical compound, such as an organic compound less than 2000 MW, an oligopeptide or polypeptide (e.g., a cytokine, an enzyme, or a protein comprising an antibody binding site), or a nucleic acid (e.g., a microRNA, an antisense nucleic acid, or a vector).

In some embodiments, the first compound is incubated with the microsphere such that the first compound is non-covalently bound to the microsphere. In other embodiments, a component that introduces a functional group to the microsphere is adhered to the microsphere, the first compound is covalently attached to the functional group.

In various embodiments of these methods, the first compound is incubated with the bead in the physiological saline solution such that the first compound is deposited on the bead along with the mineral layer coating. Such microspheres generally have the first compound deposited throughout the mineral layer coating, whereas if the compound is bound to the bead after the mineral layer is coated onto the bead, the compound would only be present on the surface of the mineral layer. The first compound would be expected to be released over a longer period of time in the former case than in the latter case.

In other embodiments, the bead is incubated in the physiological saline solution both before and after the first compound is adhered to the microsphere, after which additional first compound is adhered to the microsphere. In this case, the first compound would be internal to the surface of the mineral layer and would be released after a first compound deposited on the surface.

By controlling the addition of the compound in the above methods, a suitable release profile of the compound for any application can be achieved without undue experimentation.

Additionally, the method can further comprise incubating the microsphere with a second compound such that the second compound adheres to the microsphere. In some of these embodiments, the bead is incubated in the physiological saline solution before and after the first compound is adhered, after which the second compound is adhered to the microsphere, such that the first compound and the second compound are on different layers of the first calcium-containing mineral layer. Such a microsphere would release the second compound before the first compound.

The present application is further directed to any of the above-described microspheres made by any of the above-described methods.

The application is further directed to a method of administering a compound to a vertebrate. The method comprises administering any of the microspheres disclosed above to the vertebrate, where the microsphere further comprises the compound. In some embodiments, the microsphere is in a pharmaceutically acceptable material.

By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described microspheres can be formulated without undue experimentation for administration to a vertebrate, including humans, as appropriate for the particular application. Additionally, proper dosages of the microspheres can be determined without undue experimentation using standard dose-response protocols.

Accordingly, the microspheres may be enclosed in gelatin capsules. For the purpose of oral therapeutic administration, the microspheres of the present invention may be incorporated with excipients and used in the form of tablets, troches, capsules, elixirs, suspensions, syrups, wafers, chewing gums and the like.

The microspheres can alternatively be administered parenterally such as for example, by intravenous, intramuscular, intrathecal or subcutaneous injection. Such administration can be systemic, for example if the microspheres were administered by injection into the blood stream. Alternatively, the administration can be local, e.g., an injection of the microspheres directly onto an area where there is a tissue defect, where the compound is a cytokine that stimulates filling in the defect. Parenteral administration can be accomplished by incorporating the microspheres into a suspension. Such suspensions may also include sterile diluents such as water for injection, saline solution, fixed oils, polyethylene glycols, glycerin, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of osmolarity such as sodium chloride or dextrose may also be added. The parenteral preparation can be enclosed in ampules, disposable syringes or multiple dose vials made of glass or plastic.

Rectal administration includes administering the microspheres, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous adsorption of the microspheres to the skin. Transdermal formulations include patches (such as the well-known nicotine patch), ointments, creams, gels, salves and the like.

The present invention includes nasally administering to the vertebrate a therapeutically effective amount of the microspheres. As used herein, nasally administering or nasal administration includes administering the compound to the mucous membranes of the nasal passage or nasal cavity of the patient. As used herein, pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place by applying the microspheres in a nasal tampon or nasal sponge.

These methods can be used to treat any vertebrate, including wild or domesticated mammals or birds, including farm animals and pets. In some embodiments, the vertebrate is a human.

In various embodiments, the vertebrate has a condition that is treatable by administering the compound. Nonlimiting examples of such conditions include cancer, diabetes, Alzheimer's disease, Parkinson's disease, a heart disease, a virus infection, a bacterial infection, a parasitic infection, an autoimmune disease, an allergy, a prion disease, a gastrointestinal disease, a liver disease, a kidney disease, a skin disease, a bone disease, a congenital disease or defect, a disease characterized by insufficiency of a protein or a metabolite, erectile dysfunction or baldness.

In some embodiments, the condition is a tissue defect. The tissue defect can be, for example, in a bone, a soft tissue, or an internal organ. The defect may be caused by disease or trauma, or it may be congenital.

The application is also directed to the use of any of the above-described microspheres for the manufacture of a medicament for treating a vertebrate with a compound. In some of these embodiments the vertebrate is a mammal, e.g., a human. Further, the application is directed to the use of any of the above-described microspheres for the treatment of a vertebrate with a compound. In some of these embodiments the vertebrate is a mammal, e.g., a human.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Mineral-Coated Polymer Microspheres for Controlled Protein Binding and Release

The work described herein evaluates the hypothesis that protein-mineral interactions could be used as an alternative mechanism to create biodegradable micro-carriers for controlled protein binding and release. In particular, the calcium phosphate mineral hydroxyapatite is employed as a substrate for protein binding and release, as it has been used for over 50 years in chromatographic protein separations based on its ability to bind and release both acidic and basic proteins under particular solution conditions. Here a first demonstration is provided establishing that biodegradable polymer microspheres can be coated with an inorganic hydroxyapatite layer, and that this biodegradable coating can be used as a substrate for binding and sustained release of acidic and basic proteins.

Figure 1:
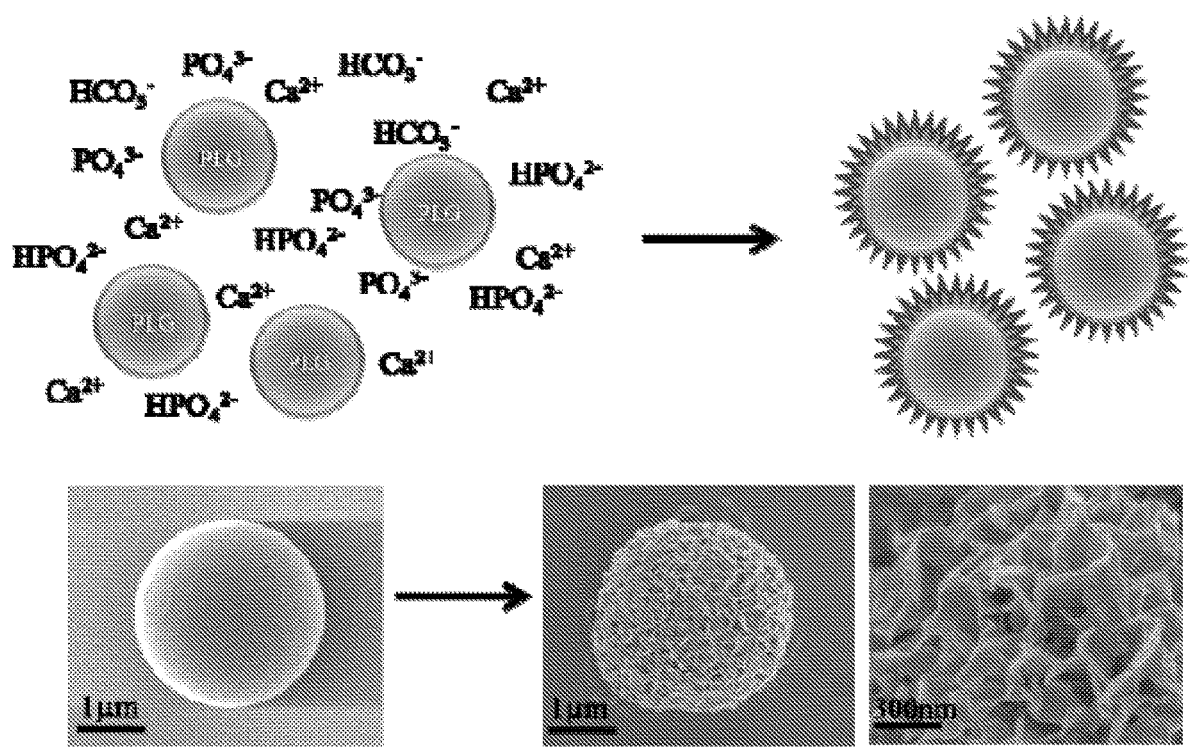
Figure 2:
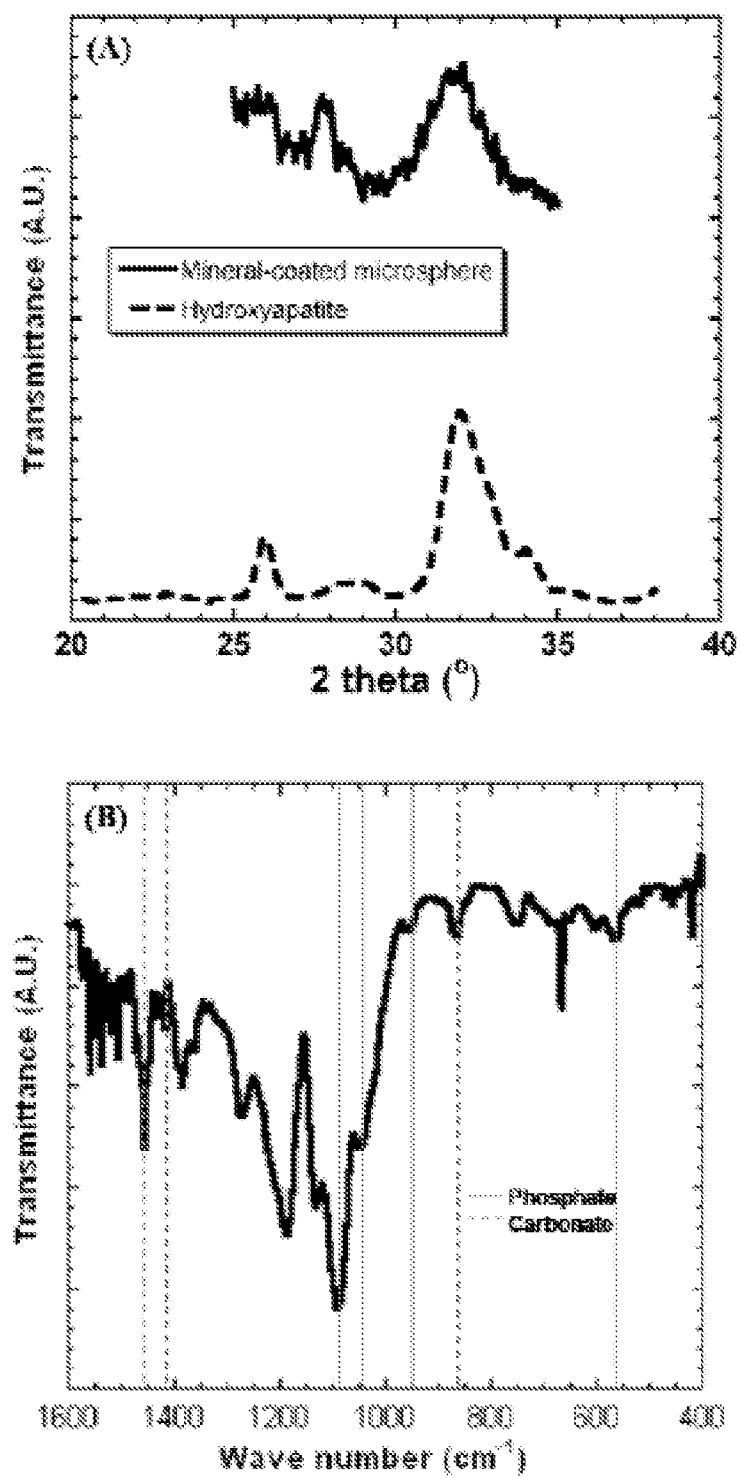

This approach involves nucleation and growth of inorganic calcium phosphate mineral coatings on the surface of organic, biodegradable polymer microspheres at near physiologic temperature and pH. This mineral growth process mimics natural biomineralization processes (Mann, 2001), and results in a mineral coating that is similar in structure (platelike nanostructure) and composition (carbonated-substituted, calcium-deficient hydroxyapatite phase) to human bone mineral, as detailed previously on macroscopic polymer films (Murphy and Mooney, 2002). Specifically, protein-releasing, mineral-coated polymer microspheres were prepared here via a two-step process involving: i) formation of biodegradable PLG microspheres using a standard water-oil-water double emulsion process (Meng et al., 2003); and ii) coating of PLG microspheres with an inorganic, bone-like mineral (BLM) film via incubation in a modified simulated body fluid (mSBF), an aqueous solution which contains the ionic constituents of blood plasma with 2-fold higher concentrations of calcium and phosphate ions (Murphy and Messersmith, 2000) (FIG. 1). X-ray diffraction and FTIR spectra indicate that the mineral grown on PLG microspheres is an apatite mineral (FIG. 2). Scanning electron microscopy (SEM) (FIG. 1) indicates that the mineral film is continuous on the microsphere surface and has a plate-like nanostructure. Therefore, the mineral layer grown on biodegradable polymer microspheres is similar in composition and morphology to bone mineral, as described previously Murphy and Mooney, 2002).

Importantly, the mineral-coated microsphere surface is porous and contains charged calcium and phosphate components. Therefore, it was hypothesized that these microspheres would be capable of efficiently binding soluble biological molecules via electrostatic interactions, in a manner analogous to the above mentioned hydroxyapatite chromatography (Urist et al., 1984; Schroder et al., 2003). In this study the possibility was examined of using mineral-coated microspheres as a carrier for two proteins with differing characteristics: i) an acidic protein, bovine serum albumin (BSA) (pI=4.7); and ii) a basic protein, cytochrome c (Cyt c) (pI=10.2). These model proteins were chosen to illustrate the influence of protein characteristics on binding efficiency and release kinetics, and because of their biological relevance. Specifically, albumin is one of the most abundant proteins found in blood plasma and has been shown to promote formation of bone tissue (Yamaguchi et al., 2003), while cytochrome c serves as a model protein for several basic growth factors, such as fibroblast growth factor-2, bone morphogenic proteins, and transforming growth factor β.

Figure 3:
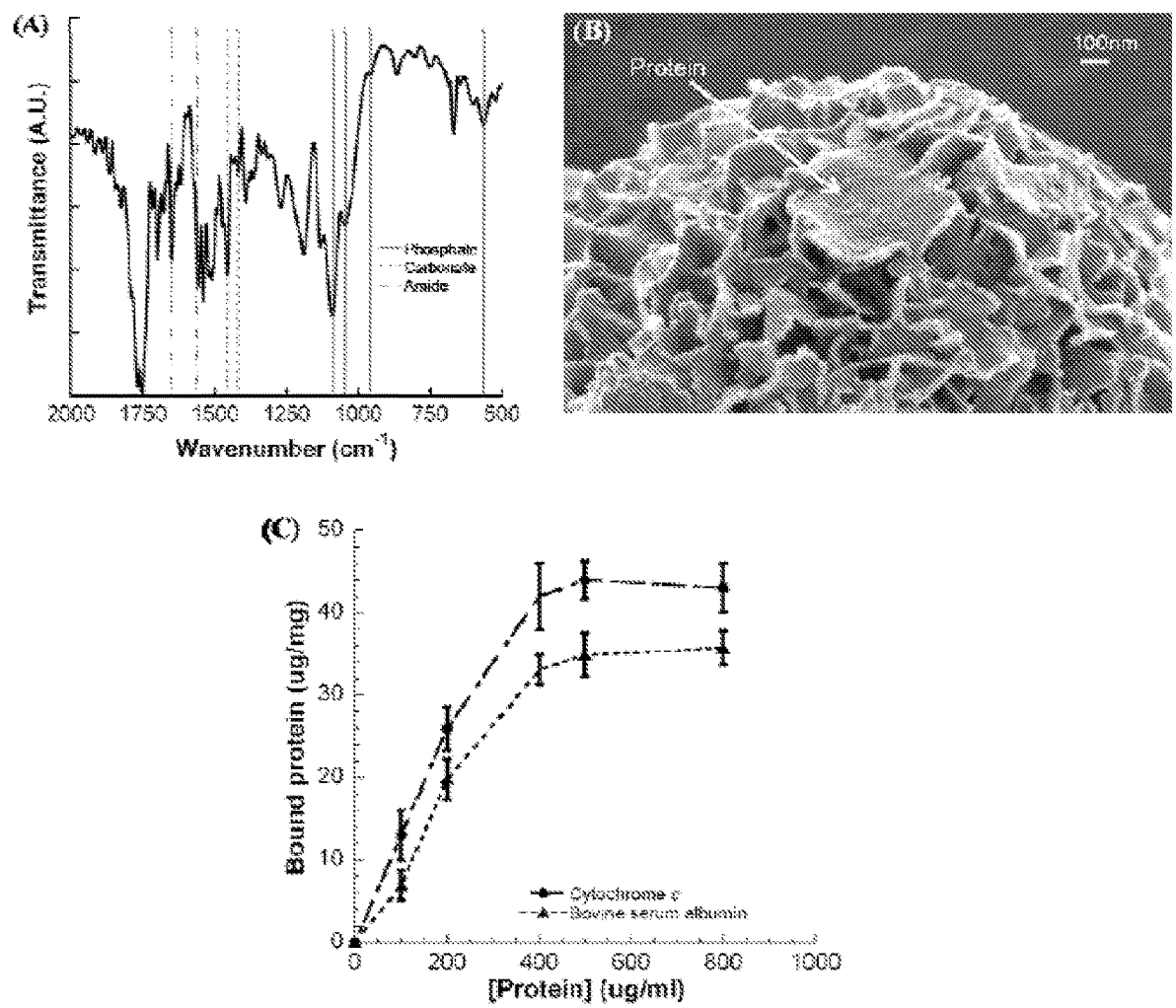

Binding of BSA on mineral-coated PLG microspheres was first detected by FTIR analysis (FIG. 3A). The FTIR spectrum shows phosphate peaks (1087, 1035, 950, and 560 $cm^{-1}$) and carbonate peaks (1456 and 1417 $cm^{-1}$) corresponding to carbonate-substituted hydroxyapatite mineral coatings, consistent with previous studies of BLM coatings formed on biodegradable polymer substrata (Murphy and Mooney, 2002). The FTIR spectrum also shows amide peaks (1653 and 1558 $cm^{-1}$) corresponding to the presence of BSA bound to the coating surface. SEM analysis corroborates the FTIR analysis, and shows bound protein deposited on mineral-coated PLG microspheres (FIG. 3B). BSA binding on the mineral coating was next quantified by incubating mineral-coated microspheres for 4 hours in PBS with varying BSA concentrations. The results show that the amount of bound BSA on the microspheres increased linearly in the range of 0-200 μg/ml and reached a plateau at 400 μg/ml (FIG. 3C). This binding is consistent with a typical Langmuir isotherm, and corroborates previous studies of BSA binding to hydroxyapatite powder (Hughes Wassell et al., 1995). Cyt c showed a binding curve similar to that of BSA, and it is noteworthy that Cyt c bound to the mineral more efficiently than BSA at the same solution protein concentrations. The enhanced binding efficiency of Cyt c is likely due to its smaller hydrodynamic radius ($RH$=0.18 nm)(Moror et al., 2001) when compared to BSA ($RH$=3.6 nm)(Boyer and Hsu, 1992). It is likely that protein binding in the current study is mediated by ionic interactions, and the presence of both positively charged calcium and negatively charged phosphate ions on the apatite mineral surface enables binding of both acidic and basic proteins at physiologic pH. This assertion is supported by recent demonstrations that the amount of bound protein on highly crystallized hydroxyapatite can be attributed to the ionic interaction between the surface charges of hydroxyapatite and proteins (Kawachi et al., 2008).

Figure 4:
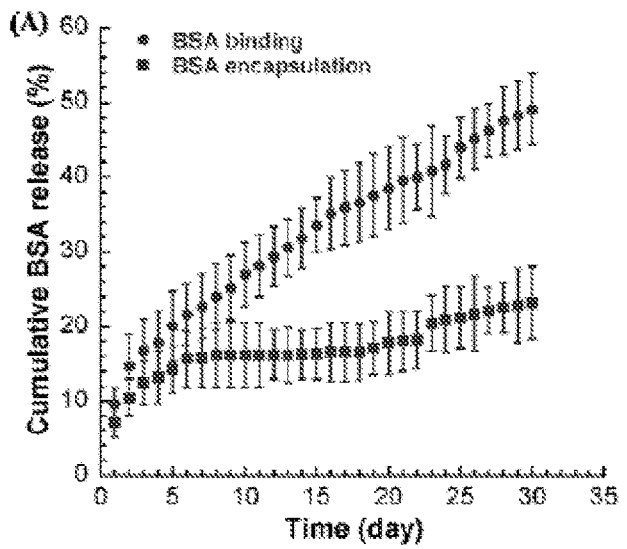
Figure 4:
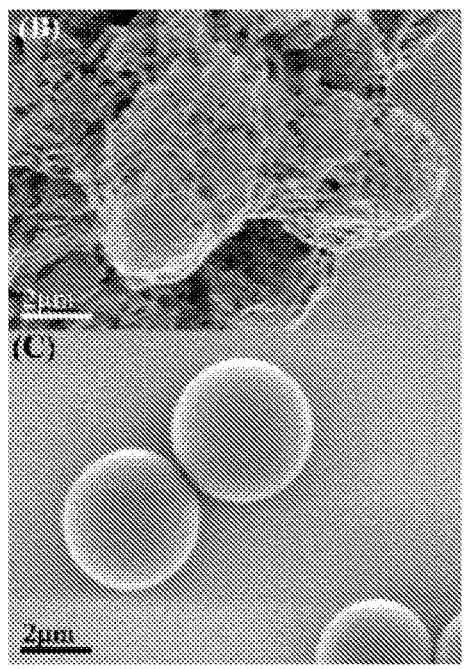
Figure 4:
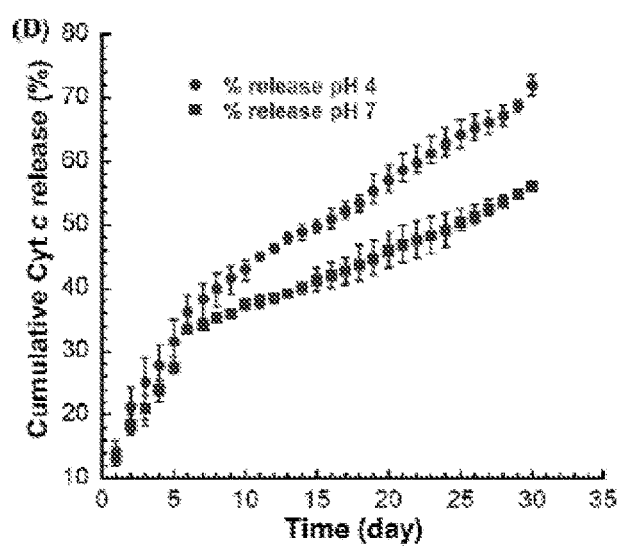
Figure 4:
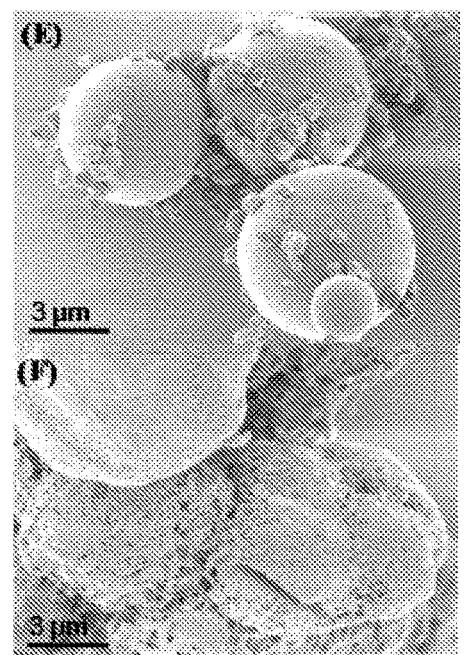

The release kinetics of BSA from mineral-coated PLG microspheres were investigated by incubating mineral-coated microspheres in phosphate-buffered saline (PBS) solution at pH 7.4 (FIG. 4A). BSA release was sustained over 30 days, and the release displayed near linear kinetics. In contrast, the cumulative release of BSA encapsulated in PLG microspheres via standard processing techniques (Meng et al., 2003) displayed a much lower level of cumulative release over 30 days, and the majority of the released protein represented a "burst" release during the initial 72 hours. More specifically, after 30 days in PBS the mineralized microspheres released 49±4.8%, while 23±4.9% of the BSA encapsulated in PLG microspheres was released over the same timeframe. SEM analysis of the mineral-coated microspheres (FIG. 4B) showed little clear evidence of mineral dissolution after 30 days of immersion in PBS. PLG microspheres with encapsulated BSA remained intact for the duration of the release experiment (FIG. 4C), as expected based on previous studies by Porjazoska et al. (2004).

To gain further insight into the factors influencing protein release from mineral-coated microspheres, Cyt c release in phosphate-citrate buffer, pH=4.0, and in PBS, pH=7.4 was characterized. After 30 days in buffers pH 4.0 and pH 7.4 the mineral-coated microspheres released 72±1.6% and 56±1.1% of Cyt c, respectively. The release profile was similar to that of BSA, with near linear, sustained kinetics over more than 30 days. The more rapid release of Cyt c at low pH can be attributed to pH-dependent mineral dissolution. SEM images of the microspheres after 30 days of release clearly show that mineral dissolution is increased at pH 4.0 when compared to pH 7.4 (FIGS. 4E and 4F). These results are in agreement with Matsumoto et al. (2004), reporting a fast release rate of Cyt c from hydroxyapatite particles at pH 4.0 as a result of an increase in the dissolution rate at low pH. Taken together, these data indicate that the dissolution of the BLM coating plays an important role in protein release, and that it may be possible in future studies to tailor protein release characteristics by varying the stability of the mineral coating. pH-dependent changes in protein release kinetics could be useful in biomedical applications, as an acidic local pH exists within important physiologic (e.g. stomach, remodeling bone tissue [Baron, 1989]) and pathologic (e.g. tumors [Vaupel et al., 1989], chronic wounds [Schmaljohann et al., 2006]) environments in vivo.

It was shown here that mineral-coated PLG microspheres can serve as effective carriers for protein binding and sustained release. The protein release profile from these minerals does not include the "burst" release that is typically observed in biodegradable microparticle release systems, and the protein release rate is dependent on protein characteristics and the local pH. It is noteworthy that previous studies using hydroxyapatite chromatography to purify proteins and DNA (Urist et al., 1984) suggest that this mechanism for protein binding and release may be adaptable to a broad range of acidic and basic biomolecules, and that the biological activity of molecules released from minerals in this manner is likely to be high. In addition, the gentle processing conditions used to form mineral coatings on biodegradable polymer microspheres suggest that several biodegradable micro- or nano-scale materials can be used as templates for mineral growth, and that biological molecules can potentially be included into mineral coatings during the course of the coating process. Therefore, this approach may represent an adaptable mechanism for biomolecule binding and controlled release for biomedical applications.

Experimental

Mineral-coated Poly(lactide-co-glycolide) (PLG) microspheres were prepared by incubating 85:15 PLG microspheres (average MW=50,000-70,000) in modified-simulated body fluid (mSBF) adjusted to 37° C. and pH to 6.8 for 7 days. The mSBF solution was refreshed daily. Samples were rinsed with distilled water and freeze dried prior SEM, XRD, FTIR spectroscopy studies.

Model Protein Binding to Mineral-Coated Microspheres:
Bovine serum albumin (BSA) and cytochrome c (Cyt c) were used as model proteins. Five mg of mineral-coated microspheres were immersed in 1.5 ml solutions containing variable protein concentrations (0-800 μg/ml, 4 hr, 37° C.).

The solution was centrifuged to sediment the microspheres, and the amount of protein in the supernatant was measured. The centrifuged microspheres were washed with distilled water and freeze dried prior to SEM and FTIR spectroscopy.

Five mg of mineral-coated microspheres were immersed in 1.5 ml of protein solutions (200 µg/ml, 4 hr, 37° C.) as described above, to produce protein-containing, mineral-coated microspheres. For BSA protein, the microspheres were immersed in phosphate buffer solution (pH=7.4, 1 ml). The resulting solution was incubated and rotated for 24 h in the incubator and the release medium was changed daily for 30 days. The amount of protein released was determined by the µBCA assay (Pierce, I L). After a 30 day incubation the microspheres were washed with distilled water and freeze dried, and their morphology was examined by SEM. For Cyt c, two different pH (7.4 and 4.0) of phosphate buffer solutions were used as the release medium. Experiments were repeated three times and results were presented as means and standard deviations from the three replicates.

Example 2

Fabrication and Characterization of Mineral-Coated Poly(Lactide-Co-Glycolide) Microspheres Example Summary Mineral-coated microspheres were prepared via a bioinspired, heterogeneous nucleation process at physiologic temperature. Poly(DL-lactide-co-glycolide) (PLG) microspheres were fabricated via a water-in-oil-in-water emulsion method and were mineral-coated via incubation in a modified simulated body fluid (mSBF). X-ray diffraction, Fourier transform infrared spectroscopy, and scanning electron microscopy with associated energy dispersive X-ray spectroscopy confirmed the presence of a continuous mineral coating on the microspheres. The mineral grown on the PLG microsphere surface was a carbonate-containing hydroxyapatite, and the mineral shows a porous structure of plate-like mineral crystals at the nanometer scale. Aggregation of mineral-coated microspheres was observed when microsphere concentrations above 0.50 mg/mL were incubated in mSBF for 7 days, and the size of aggregates was dependent on the microsphere concentration in solution. In vitro mineral dissolution studies performed in Tris-buffered saline confirmed that the mineral formed was resorbable. A surfactant additive (Tween 20™ [PEG(20)sorbitan monolaurate]) was incorporated into mSBF to prevent microsphere aggregation during the mineral growth process, and Tween 20™ not only prevented aggregation, but also influenced the characteristics of the mineral formed on the surface of PLG microspheres. These findings indicate that mineral-coated PLG microspheres can be synthesized in a controlled fashion using a bioinspired process. These materials could be useful in a range of applications, including controlled drug delivery and biomolecule purification.

Introduction

Although they have been extensively studied in orthopedic implant design and bone tissue engineering applications, mineral-coated biomaterials have not been applied as extensively in microscale applications, such as drug delivery and molecular separations.

An important property of hydroxyapatite is the ability to bind to biological molecules. For example, hydroxyapatite is commonly used as a resin for chromatographic purification of proteins and plasmid DNA (Colman et al., 1978; Schroder et al., 2003), as the mineral surface contains both positive ($Ca^{2+}$) and negative ($PO_4^{3-}$) ions capable of interacting electrostatically with basic and acidic molecules, respectively. This ability to bind, and subsequently release, biological molecules has recently been used as a mechanism for sustained drug delivery (Example 1). Therefore, a large body of work has focused on creating bone-like hydroxyapatite coatings on polymeric biomaterials to simultaneously exploit both the bulk properties of biodegradable polymers and the bioactivity of hydroxyapatite coatings.

Here it was hypothesized that biodegradable polymer microspheres, which are commonly used in drug delivery applications, could be coated with a biodegradable, hydroxyapatite mineral using a bioinspired mineral nucleation and growth process. The resulting materials are designed to exploit the controllable properties of polymer microspheres (e.g. size, size range, degradability, drug incorporation), while also taking advantage of the biological properties of the mineral layer (e.g. bioactivity, biomolecule binding/incorporation). In this study mineral-coated microspheres were fabricated using a two-step processing route. First, poly(lactide-co-glycolide) (PLG) microspheres were fabricated using a double emulsion method, then those microspheres were incubated in modified simulated body fluid, allowing for mineral nucleation and growth in near physiological conditions. The amount of mineral formed can be controlled by the incubation time and the concentration of microspheres in solution. A surfactant additive influenced microsphere aggregation and the morphology of the mineral formed. The results presented here illustrate that an inorganic mineral layer can be grown in a controllable manner on the surface of biodegradable microspheres, and these materials may find utility in a range of biomedical applications, most notable drug delivery and chromatography.

Experimental Section

Microsphere Fabrication.

85:15 PLG (average MW=50,000-70,000) and polyvinyl alcohol (PVA, MW 9-10 kDa) were obtained from Sigma-Aldrich (St. Louis, Mo.). All chemicals and solvents were of reagent grade and were obtained from Fisher Chemicals (Fair Lawn, N.J.).

PLG microspheres were fabricated by water-in-oil-in-water (W/O/W) double emulsion technique as reported elsewhere (Berchane et al., 2006). Briefly, the organic phase consisted of 5% (w/v) PLG in 1 ml ethyl acetate. The aqueous phase consisted of 0.1 ml phosphate buffered saline (PBS). The aqueous and organic phases were mixed and sonicated using Sonifier 250 (VWR International, Inc., West Chester, Pa.) for 15 s. The resulting first emulsion was added immediately into 1 ml of aqueous 1% (w/v) PVA in 7% (v/v) ethyl acetate that was being mechanically vortexed for 15 s to form a second emulsion. The resulting solution was then added to a beaker containing 200 ml of 0.3% PVA in 7% ethyl acetate and further rigorously stirred for 4 hr to allow for organic solvent evaporation. The resulting microspheres were collected by filtration through 0.22 µm filter, washed three times with de-ionized water, and resuspended in de-ionized water. The microspheres were lyophilized for a minimum of 48 hr and were stored at −20° C. in the presence of a desiccant.

To confirm that PLG microspheres were negatively charged in physiological buffers, the $\zeta$ potential of PLG microspheres was first characterized in PBS and mSBF solutions. The surface charge of the microsphere particles was measured with a Zetasizer 3000HS (Malvern Instruments, Worcestershire, U.K.). The electrophoretic mobility of uncoated microspheres in three 6 mL aliquots was measured to determine the surface potential, with each injection having five measurements. Samples were syringe-loaded and measured at 25° C. in 1×PBS or mSBF, at a pH of 6.8 to mimic mineral coating conditions.

Quantification of aggregated microspheres in various buffers was performed by incubating a 0.5% (w/v) PLG microsphere in a selected buffer (1×PBS, mSBF, and mSBF+0.1% (v/v) Tween 20™) for 1, 3, and 7 days. The suspension was held at 37° C. and rotated continuously for the duration of the study period, identical with the conditions used for mineral growth. Prior to changing the buffer on the subsequent day, aliquots of each condition were taken, diluted 1:8, and imaged under an Olympus 1×51 light microscope at 20× magnification. Four photographs were taken per sample per time point with a Hamamatsu 1394 ORCA-285 camera. The resultant images were viewed and counted using Image J software.

Mineral Coating of Microsphere.

PLG microspheres were coated with a mineral layer via incubation in a modified simulated body fluid (mSBF). The mSBF solution was replaced daily to ensure adequate ion concentrations for mineral growth. mSBF possesses inorganic ion concentrations similar to those of human blood plasma, with 2× the concentration of calcium and phosphate ions. mSBF was prepared by dissolving 141 mM NaCl, 4.0 mM KCl, 0.5 mM $MgSO_4$, 1.0 mM $MgCl_2$, 4.2 mM $NaHCO_3$, 5.0 mM $CaCl_2$, and 2.0 mM $KH_2PO_4$ in distilled water, buffered to pH 6.8, and was held at 37° C. for the duration of the incubation period. In some experiments, 0.1% of Tween 20™ (Sigma-Aldrich, St. Louis, Mo.) was added to the mSBF to prevent the aggregation of microspheres.

Materials Characterization.

The composition and phase of the minerals grown on polymer microspheres were analyzed using a HI-STAR 2D x-ray diffractometer (Siemen Corporation, NY) operating at 40 kV and 20 mA. X-ray diffraction spectra were taken for 2θ=20-40° and data collection was controlled using General Area Detector Diffraction System (GADDS) version 4.0 (Bruker AXS Inc., Madison, Wis.).

Fourier transform infrared spectroscopy (FTIR) data were obtained using EQUINOX 55 spectrometer (Bruker AXS Inc., Madison, Wis.). Samples were examined in transmission mode in the 400-4000 $cm^{-1}$ range and data were analyzed by OPUS software.

The morphology and composition of the coated mineral on the microsphere surface was analyzed using scanning electron microscopy (SEM) with energy-dispersive X-ray spectroscopy (EDS). Microspheres before and after mSBF incubation were mounted on aluminum stubs with double sided carbon tape, sputtered with gold for 30 s at 45 mA and characterized using a LEO DSM 1530 field emission SEM, operating at 2 kV for SEM and 10 kV for EDS.

Dissolution of mineral coatings was characterized by measuring release of $PO_4^{3-}$ and $Ca^{2+}$ over 25 days in multiple solutions, including tris-buffered saline (150 mM NaCl and 20 mM Tris, pH=7.4) or Dulbecco's Modified Eagle Medium (DMEM) without L-glutamine and phenol red (Mediatech, Inc., Manassas, Va.). The buffer was collected and refreshed daily. The study was performed in triplicate and held at 37° C. for the duration of dissolution study period.

The amount of phosphate released from mineral-coated microspheres was analyzed colorimetrically using an assay previously reported (Heinonen and Lahti, 1981). Briefly, a working AAM (acetone-acid-molybdate) solution was prepared by mixing 2 parts acetone with 1 part 5 N sulfuric acid, and 1 part 10 mM ammonium molybdate solution. The assay was performed in a 96-well plate by adding 100 μl a freshly made working solution to 100 μl sample. The amount of phosphate complex was quantitatively detected by measuring the absorbance at 405 nm on a Synergy™ HT Multidetection Microplate Readers (Bio-Tek Instruments, Inc., UK) and comparing to a set of standards with known phosphate concentrations.

$Ca^{2+}$ release was direct measured using QuantiChrom™ Calcium Assay Kit (DICA-500) (BioAssay Systems, Hayward, Calif.). A phenolsulphonephthalein dye forms a very stable blue color complex with free calcium. The intensity of the complex, measured via absorbance at 612 nm, was used to measure released $Ca^{2+}$ by comparing to a set of standards with known calcium concentrations. Dissolution experiments were performed in triplicate and statistical analyses for calcium and phosphate release were carried out using ANOVA.

Results and Discussion

Formation of Mineral-Coated Microspheres.

Figure 5:
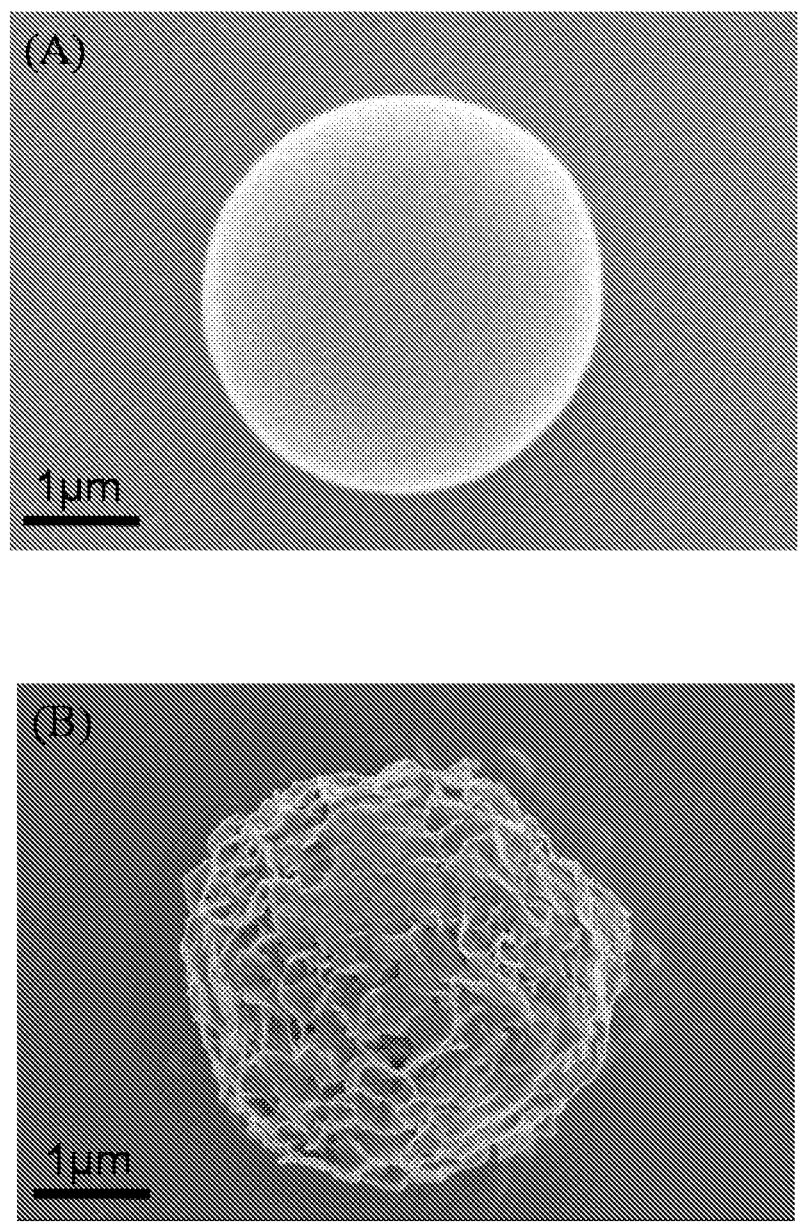
Figure 6:
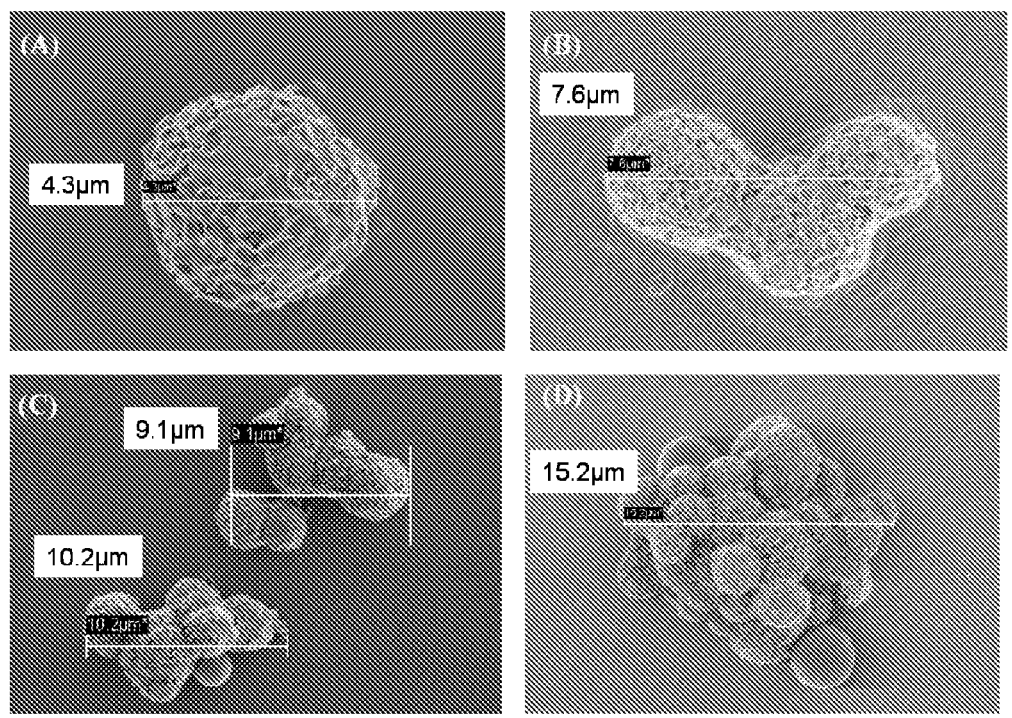
Figure 6:
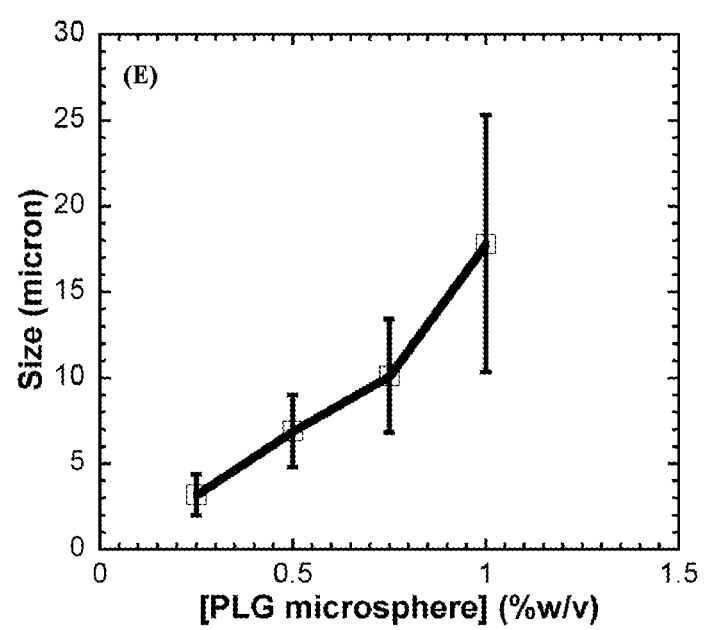

The formation of mineral-coated microspheres involved a two-step process. First, PLG microspheres were fabricated by an established water-in-oil-in-water emulsion method followed by a mineral nucleation and growth process performed in mSBF solution. Incubation of PLG microspheres in mSBF led to nucleation and subsequent growth of a hydroxyapatite mineral coating on the microsphere surface (FIG. 5). SEM observation showed that the nanocrystallites grown on the microsphere surface exhibit a plate-like morphology (FIG. 5B), similar to the morphology observed in previous studies (Luont et al., 2006; Jabbarzadeh et al., 2007). Micrographs of the microspheres incubated in mSBF for 7 days show continuous mineral coatings on individual microspheres incubated at 0.25% and 0.50% (w/v) (FIG. 6A, B). Microsphere aggregation was observed as microspheres concentration increased, and mineral coatings were observed on the surface of microsphere aggregates (FIG. 6B, C, D).

Figure 7:
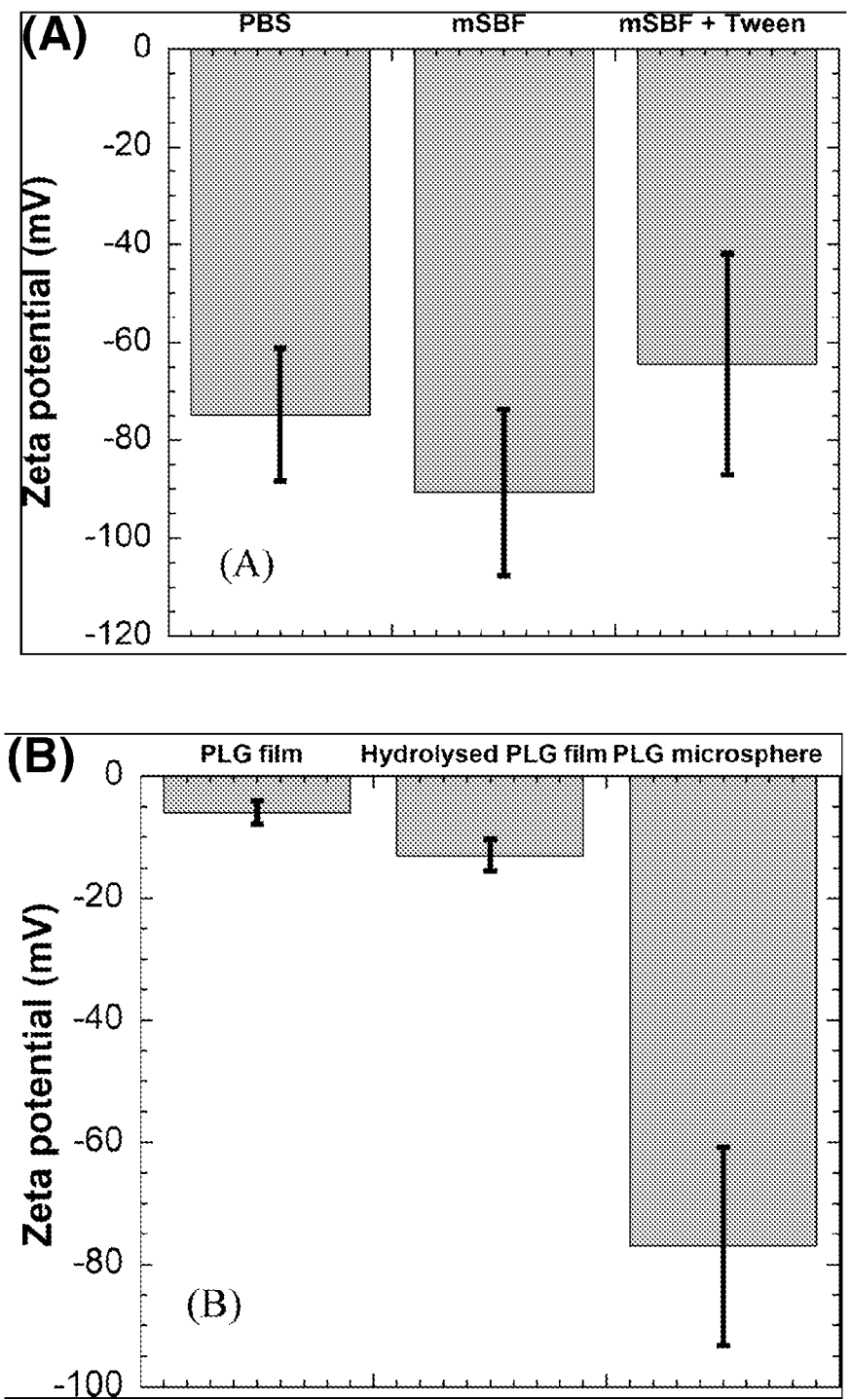
FIG. 7 is a graph showing the ζ potential of PLG microspheres in buffers PBS, mSBF, and mSBF+0.1% (v/v) Tween 20™ (Panel A) and nonhydrolyzed and hydrolyzed PLG films in comparison with PLG microspheres (Panel B).

The ζ potential of these particles in PBS (−81.09 [7.71 mV]) and mSBF (−78.62 [15.91 mV]) indicated that the particles were negatively charged (FIG. 7). These ζ potential values are consistent with previous studies of PLG microspheres, which have also shown that PLG microspheres have negatively charged surface carboxylate groups (Eniola et al., 2002) and that they have ζ potential values ranging from −22 to −80, depending on the microsphere preparation technique and the testing buffer (Fischer et al., 2006; Chesko et al., 2005; Mu and Feng, 2001; Coombes et al., 1997). The presence of carboxylate groups on the surface of these microspheres is important because previous studies have indicated that these groups are capable of promoting heterogeneous mineral nucleation and growth. However, in previous studies, PLG materials were hydrolyzed to produce surfaces containing carboxylate ions, while in this case, the PLG microsphere surfaces included negatively charged groups when synthesized via double-emulsion processing without additional hydrolysis. Interestingly, the ζ potential of PLG microspheres was significantly lower than that of hydrolyzed PLG films used previously as templates for bioinspired mineral nucleation and growth (FIG. 7B) (Murphy and Mooney, 2002), suggesting that the microspheres may serve as advantageous templates for mineral growth.

ζ potential results showed charged microspheres in all buffers tested (FIG. 7A), so it is possible that the presence of salt leads to shielding of the microsphere surface charge, thereby limiting electrostatic repulsion and facilitating aggregation.

Characteristics of Mineral Coatings.

Figure 8:
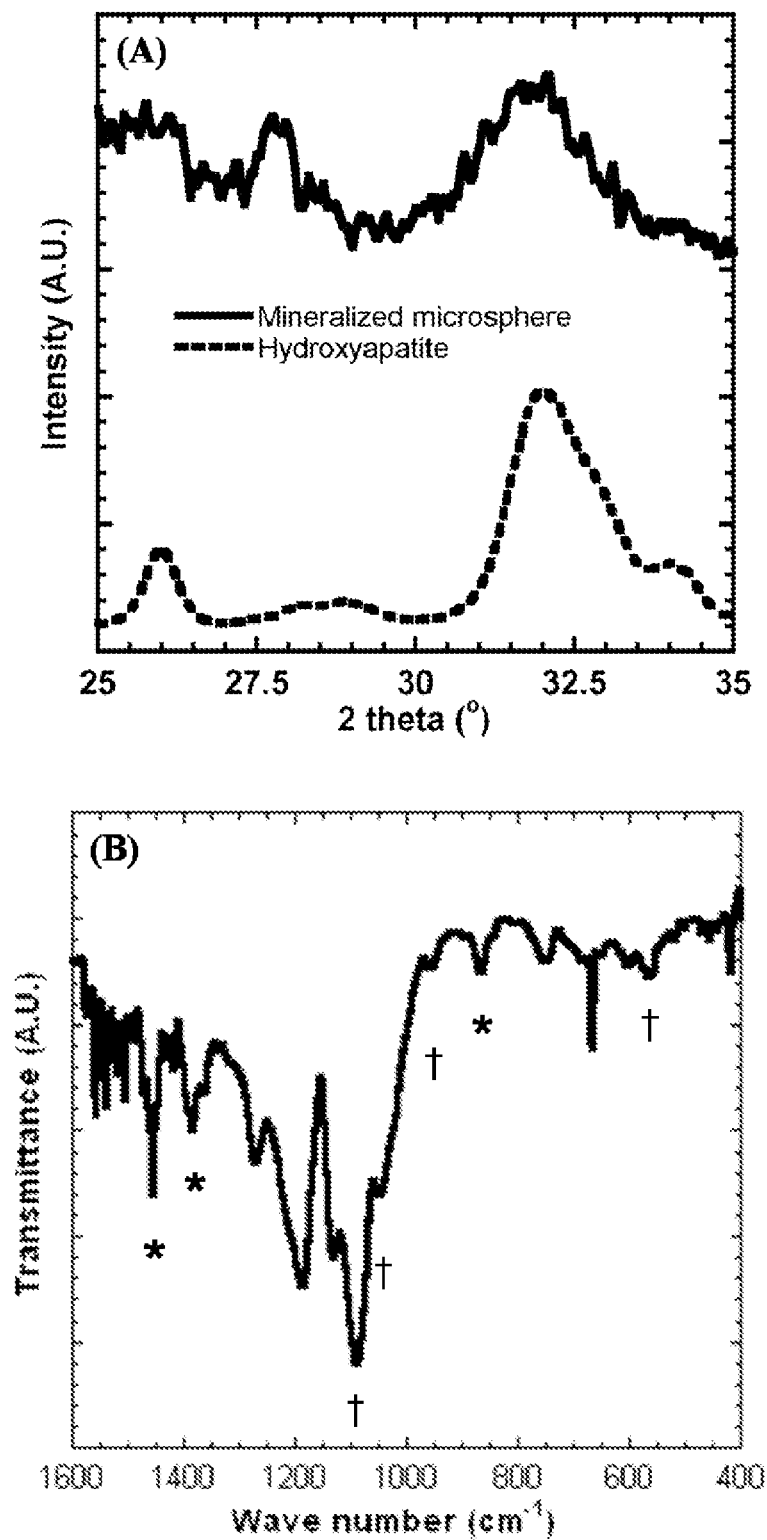
FIG. 8 is graphs showing X-ray diffraction analysis of mineral-coated microspheres and hydroxyapatite powder (included for comparison) (Panel A), and Fourier transform infrared analysis of mineral-coated microspheres (Panel B). Peaks associated with carbonate are denoted by *, and peaks associated with phosphate are denoted by †.

The phase and composition of mineral coatings on PLG microspheres after a 7 day incubation in mSBF were characterized by XRD and FTIR. XRD spectra of mineral-coated microspheres show three characteristic hydroxyapatite peaks at 2θ=25.87°, 28.68°, and 32.05° similar to the peaks present in the XRD spectrum of reagent grade hydroxyapatite powder (Sigma-Aldrich, St. Louis, Mo.) at 2θ=26°, 28.5°, and 32° (FIG. 8A). The peak areas in the XRD spectrum of mineral-coated microspheres are broader than that of hydroxyapatite powder, and this may be due to the small crystal size of the mineral deposited on the PLG microsphere surfaces. FTIR peaks observed in the 1600-400 cm$^{-1}$ region can be attributed to carbonate-substituted hydroxyapatite, including phosphate peaks at 570, 950, 1046, and 1098 cm$^{-1}$, and carbonate peaks at 870, 1410, and 1456 cm$^{-1}$ (FIG. 8B). These results are consistent with previous studies on growth of carbonate-substituted hydroxyapatite mineral on PLG films (Murphy et al., 2000; Qui et al., 2000).

Figure 9:
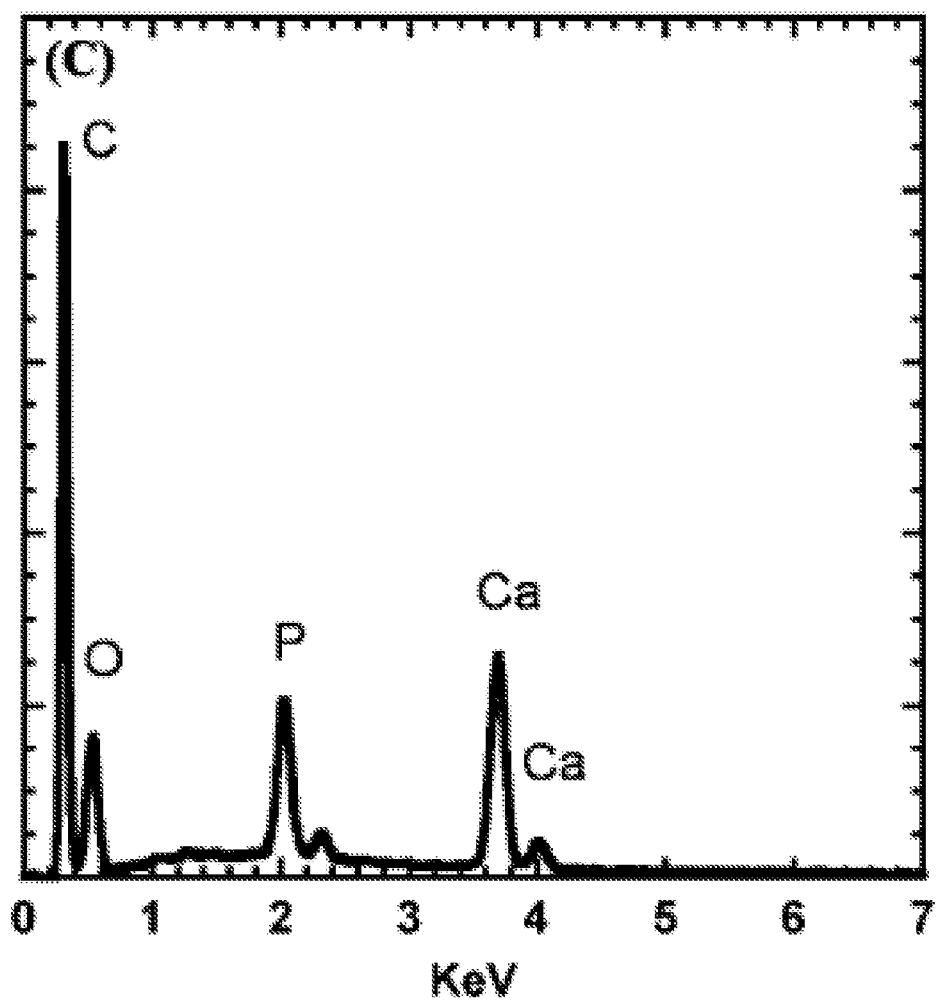
FIG. 9 shows an EDS spectrum of mineral-coated microspheres after a 7 day incubation in mSBF.

The EDS spectrum also confirms the presence of calcium and phosphorus on the mineral-coated microspheres (FIG. 9). The Ca/P ratio of the mineral coating was 1.41 after 7 days of incubation in mSBF, which is consistent with that of previous studies of biological apatites (Elliott, 1994) and bioinspired mineral coatings (Jabbarzadeh et al., 2007).

Time lapse SEM analyses of PLG microspheres at various times during mSBF incubation provide some insight into the mechanism of nucleation and growth of carbonate apatite mineral on aggregating microspheres (FIG. 10). The nucleation process begins during the first three days of incubation in mSBF (FIG. 10A, B). During this stage the aggregation of microsphere begins to occur. As the microspheres begin to aggregate, small crystals (~2-10 nm) begin to form at the interface between microspheres (FIG. 10A, B), perhaps due in part to local supersaturation of surface functional groups and associated mineral ions at the interface. After five days a highly porous structure of plate-like hydroxyapatite crystals appear on the surfaces of aggregated microspheres (FIG. 10C), ultimately growing into a continuous coating (FIG. 10D). The size of the aggregates depends on the initial concentration of microspheres in solution (FIG. 6E), suggesting a potential mechanism for control over the size of coated aggregates. Mineral coatings were also observed on the surface of microsphere aggregates. Other analyses not presented here suggest that the efficiency of microsphere mineralization increases in conditions that promote microsphere aggregation. Our time-course analysis of mineral formation in solutions with higher concentrations of microspheres (FIG. 10) also demonstrates that mineral nucleation can occur at the interface between aggregated microspheres (e.g., FIG. 10B), which suggests that mineral formation can be facilitated by aggregation.

To determine whether the aggregation of the microspheres was due to some intrinsic property of mSBF, we performed aggregation experiments in which microspheres were incubated in three different solutions: (1) a 1×PBS solution (calcium-deficient), (2) mSBF, and (3) mSBF in the presence of Tween 20™. Each incubation was performed at 37° C. with daily solution changes for 7 days. Results showed that 35% and 42% microspheres aggregated after the first day of incubation in PBS and mSBF, respectively. The percentage of aggregated microspheres increased to 87% in PBS and 90% in mSBF after 7 days of incubation. In contrast, the number of microspheres aggregated in mSBF supplemented with Tween 20™ was significantly lower at each time point (FIG. 11). These data indicate that mSBF does not significantly increase microsphere aggregation when compared to PBS and the presence of Tween 20™ significantly decreases microsphere aggregation.

Interestingly, the formation of mineral described here is analogous to previous work by He et al. (2003) on bioinspired formation of mineral in the presence of dentin matrix protein. In addition, the morphology and composition of mineral described here is similar to the apatite crystals found in human woven bone and mineralized dentin (Su et al., 2003), specifically a platelike nanostructure (FIGS. 5B and 14B), a hydroxyapatite phase (FIGS. 8A and 9), and carbonate substitution (FIG. 8B).

Dissolution and re-precipitation are key characteristics of hydroxyapatite coatings, particularly in orthopedic implant design and drug delivery applications. Some forms of hydroxyapatite mineral have been shown to degrade slowly or incompletely over extended timeframes, and the permanent presence of these materials in vivo is undesirable in applications that call for material degradation over time (e.g. tissue engineering, drug delivery). In addition, mineral dissolution can influence release of biological molecules from these coatings in drug delivery applications, as described in Example 1. Therefore, in this study dissolution of mineral coatings in Tris-buffered saline (TBS) and in DMEM was characterized for 25 days. $Ca^{2+}$ and $PO_4^{3-}$ were gradually released from mineral coatings over time in TBS (FIG. 12A), indicating that these coatings are less stable than pure, stoichiometric hydroxyapatite characterized in previous studies (Fazan and Marquis, 2000; Lin et al., 2001). The total amounts of $Ca^{2+}$ and $PO_4^{3-}$ released after 25 days in TBS were 15.87 and 10.26 μMol, respectively, and the dissolution data indicated a Ca/P mole ratio in the range of 1.37-1.61 during the course of the 25 day study. SEM images obtained at the end of the dissolution study also confirm near complete resorption of the mineral coating in TBS (FIG. 12B). The increased dissolution rate of these coatings when compared to pure hydroxyapatite coatings used in clinical applications can be explained by differences in crystallinity and carbonate substitution in the mineral. Fazan and Marquis (2000) reported previously that the dissolution rate of plasma-sprayed hydroxyapatite coatings decreases with an increase in the degree of crystallinity of the hydroxyapatite. In addition, it has been reported that incorporation of sodium and carbonate ions into calcium phosphate minerals, such as hydroxyapatite, dramatically increases the dissolution rate (Driessens et al., 1978), and the FTIR analyses described herein clearly indicate the presence of carbonate ions in the mineral coatings (FIG. 8B).

When mineral-coated microspheres were incubated in serum-free DMEM, there was a decrease in the cumulative amount of $(PO_4)^{3-}$ in the dissolution media over time (FIG. 12B), indicating that phosphate-containing mineral could possibly be re-precipitating on the surface of the mineral coating due to the ion exchange between the carbonate-substitute hydroxyapatite and the $(PO_4)^{3-}$ in DMEM. This result suggests that the mineral coating could serve as a substrate for nucleation of a calcium phosphate mineral component in the DMEM solution (FIG. 12D). The morphology of the mineral coating after incubation in DMEM was similar to the morphology of the mineral prior to incubation in DMEM, which indicates that if re-precipitation is occurring, it is resulting in growth of a new mineral phase that is similar to the mineral phase grown initially. These results are consistent with previous work, in which hydroxyapatite was immersed in either TBS or a modified Hank's-buffered saline (HBS) solution, which had an ionic composition similar to human plasma. In Tris buffer there was no new mineral formed on the hydroxyapatite surface, while in the modified HBS solution an apatite coating was grown on the surface, and the new mineral coating had a similar morphology to the initial hydroxyapatite surface (Lin et al., 2001).

Previous studies have shown that drug release kinetics from the surface of hydroxyapatite are comparable to the hydroxyapatite mineral dissolution kinetics (Jongpaiboonkit et al., 2009; Ruhe et al., 2005). Therefore, the aggregation of the mineral-coated microspheres is likely to slow drug release because of the reduction in the surface area. Multiple recent studies have shown that protein release kinetics from the surface of hydroxyapatite strongly depend on the pH of the buffer medium (Jongpaiboonkit et al., 2009; Matsumoto et al., 2004). For example, Matsumoto et al. (2004) demonstrated that enhanced mineral dissolution at low pH can lead to increased protein release. On the basis of these previous studies, we hypothesized that the composition and pH of buffer media would have an impact on the dissolution rate of the mineral. This hypothesis is supported by our data, indicating that the mineral dissolution rate is highly impacted when mineral-coated microspheres are incubated in either TBS or DMEM (FIG. 12A, B). Ions were gradually released from the mineral over time in TBS (FIG. 12A), whereas reprecipitation of the mineral occurred in phosphate-containing media (FIG. 9B). This newly deposited mineral could interfere with drug diffusion out of the initially coated mineral, thereby slowing drug release.

Effect of Surfactant on Mineral Nucleation and Growth.

In order to prevent the aggregation of microspheres during mineral nucleation and growth, Tween 20™ was added to the mSBF solution. Tween 20™ is a common surfactant used as a stabilizer in studies which measure drug release from PLG microspheres in vitro (He et al., 2005; Raman et al., 2005). The rate of mineral formation on the surface of microspheres in the presence of Tween 20™ (FIG. 10A-D) is clearly slower than in the absence of surfactant (FIG. 5, 6). FTIR spectra of the mineral formed in the presence of surfactant (FIG. 13E) show peaks in the range of 650-800 and 1108-1414 $cm^{-1}$, which indicate the presence of $PO_4^{3-}$ similar to both the mineral formed in the absence of surfactant (FIG. 8B) and synthetic HA (FIG. 13E). The FTIR spectrum also included $CO_3^2$ peaks at 1410, and 1450 $cm^{-1}$ which were absent in synthetic HA (FIG. 13E). Importantly, the morphology of the mineral coatings in the presence of surfactant differs significantly from the plate-like morphology apparent in the coatings formed without surfactant (FIG. 14). This result suggests that surfactant addition could be used as a mechanism to vary mineral morphology on the microsphere surface, which could have implications for mineral degradation, binding of biological molecules, and biological activity. For example, a rough surface with a relatively well-distributed mineral coating has an increased surface area, and the corresponding increase in available binding sites could result in higher protein binding (Example 1; LeGeros, 2002). Laurencin et al. showed that mineral coating of a sintered PLG microsphere scaffold in mSBF increase the protein adsorption capacity and decreased the initial burst release of protein from the polymer scaffold when compare to non-mineralized scaffolds (Jabbarzadeh et al., 2007).

CONCLUSION

Mineral-coated PLG microsphere have been fabricated by a simple and inexpensive two-step process involving microsphere fabrication via double emulsion and coating of those microspheres with mineral by immersing in mSBF solution. XRD and FTIR spectra indicated that the coatings comprised a carbonated-substituted hydroxyapatite mineral with a porous, plate-like nanoscale morphology. The size of the mineral-coated microspheres or microsphere aggregates can be controlled by varying the microsphere concentration in the mSBF solution. Hydroxyapatite coatings were degradable in tris-buffered saline, and the quantitative analysis of calcium and phosphate release from the coatings indicate that the Ca/P molar ratio in the mineral is consistent with that of carbonated-substituted hydroxyapatite. The presence of a surfactant during the mineral growth process delayed the formation of mineral, and also significantly affected the morphology of the mineral. Taken together, these findings indicate the feasibility of processing mineral-coated PLG microspheres in a controlled fashion using a bioinspired process. This material may be useful in a variety of applications that may benefit from the bulk properties of polymer microspheres and the surface properties of hydroxyapatite minerals, including tissue engineering, drug delivery, and biomolecule purification.

REFERENCES

Akhtar, S.; K. L. Lewis, Int. J. Pharm. 1997, 151, 57.

Bajpai, A. K.; Singh, R., Studly of biomineralization of poly(vinyl alcohol)-based scaffolds using an alternate soaking approach. Polymer International 2007, 56, (4), 557-568.

Baron, R., Anat. Rec. 1989, 224, 317.

Barrere, F.; Snel, M. M. E.; van Blitterswijk, C. A.; de Groot, K., Nano-scale study of the nucleation and growth of calcium phosphate coating on titanium implants. Biomaterials 2004, 25, (14), 2901-10.

Berchane, N. S.; Jebrail, F. F.; Carson, K. H.; Rice-Ficht, A. C., Andrews, M. J., About mean diameter and size distributions of poly(lactide-co-glycolide)(PLG) microspheres. Journal of Microencapsulation 2006, 23, (5), 539-52.

Boyer, P. M.; J. T. Hsu, AIChE J. 1992, 38, 259.

Chesko, J.; Kazzaz, J.; Ugozzoli M.; O'Haga, D. T.; Singh, M. J., Pharm. Sci. 2005, 94, 2510-2519.

Colman, A.; Byers, M. J.; Primrose, S. B.; Lyons, A., Rapid purification of plasmid DNAs by hydroxyapatite chromatography. European Journal of Biochemistry 1978, 91, 303-10.

Coombes, A. G. A.; Tasker, S.; Lindblad M.; Holmgren, J.; Hoste, K.; Toncheva, V.; Schacht, E.; Davies, M. C.; Illum, L.; Davis, S. S., Biomaterials 1997, 18, 1153-1161.

DeFail, A. J.; Edington H. D.; Matthews S.; Lee W.-C. C.; Marra K. G., J. Biomed. Mater. Res. Part A 2006, 79A, 954.

Driessens, F. C. M.; van Dijk, J. W. E.; Borggreven, J. M. P. M., Biological calcium phosphates and their role in the physiological of bone and dental tissue. I. Composition and solubility of calcium phosphates. Calcif. Tissue Res. 1978, 26, 127-37.

Ducheyne, P.; Qui, Q.-Q., Bioactive ceramics: The effect of surface reactivity on bone formation and bone cell function. Biomaterials 1999, 20, 2287-303.

Eniola, A. O., Rodgersa, S. D., Hammer, D. A., Biomaterials 2002, 23, 2167-2177.

Elliott, J. C. Structure and chemistry of the apatites and other calcium orthophosphates; Elsevier: New York, 1994.

Fazan, F.; Marquis, P. M., Dissolution behavior of plasma-sprayed hydroxyapatite coatings. Journal of Materials Science-Materials in Medicine 2000, 11, (12), 787-92.

Fernandez-Pradas, J. M.; Sardin, G.; Cleries, L.; Serra, P.; Ferrater, C.; Morenza, J. L., Deposition of hydroxyapatite thin films by excimer laser ablation Thin Solid Films 1998, 317, 393-6.

Ferreira, L., T. Squier, H. Park, H. Choe, D. S. Kohane, R. Langer, Adv. Mater. 2008, 20, 2285.

Fischer, S., Forerg, C., Ellenberger, S., Merkle, H. P., Gander, B. J. Controlled Release 2006, 111, 135-144.

Gao, Y.; Koumoto, K., Bioinspired ceramic thin film processing: Present status and future perspectives. Crystal Growth & Design 2005, 5, (5), 1983-2017.

Gledhill, H. C.; Turner, I. G.; Doyle, C., In vitro dissolution behavior of two morphologically different thermally sprayed hydroxyapatite coatings. Biomaterials 2001, 22, 695-700.

Green, D. W.; Mann, S.; Oreffo, R. O. C., Mineralized polysaccharide capsules as biomimetic microenvironments for cell, gene, and growth factor delivery in tissue engineering. Soft Matter 2006, 2, 732-7.

Habibovic, P.; Sees, T. M.; van den Doel, M. A.; van Blitterswijk, C. A.; de Groot, K., Osteoinduction by biomaterials-Physicochemical and structural influences. Journal of Biomedical Materials Research Part A 2006, 77A, (4), 747-62.

He, G.; Dahl, T.; Veis, A.; George, A., Nucleation of apatite crystals in vitro by self-assembled dentin matrix protein, 1. Nature Materials 2003, 2, (8), 552-558.

He, G.; Gajjeraman, S.; Schultz, D.; Cookson, D.; Qin, C. L.; Butler, W. T.; Hao, J. J.; George, A., Spatially and temporally controlled biomineralization is facilitated by interaction between self-assembled dentin matrix protein 1 and calcium phosphate nuclei in solution. Biochemistry 2005, 44, (49), 16140-16148.

Heinonen, J. K.; Lahti, R. J., A new and convenient colorimetric determination of inorganic orthophosphate and its application to the assay of inorganic pyrophosphatase. Analytical Biochemistry 1981, 113, 313-7.

Hong, L.; Wang, Y. L.; Jia, S. R.; Huang, Y.; Gao, C.; Wan, Y. Z., Hydroxyapatite/bacterial cellulose composites synthesized via a biomimetic route. Materials Letters 2006, 60, (13-14), 1710-1713.

Hughes Wassell, D. T., R. C. Hall, G. Embery, Biomaterials 1995, 16, 697.

Jabbarzadeh, E.; Nair, L. S.; Khan, Y. M.; Deng, M.; Laurencin, C. T., Apatite nano-crystalline surface modification of poly(lactide-co-glycolide)sintered microsphere scaffolds for bone tissue engineering: implications for protein adsorption. Journal of Materials Science-Polymer Edition 2007, 18, (9), 1141-52.

Jang, J.-H., L. D. Shea, J. Control. Release 2003, 86, 157.

Jiang, W., S. P. Schwendeman, J. Pharm. Sci. 2001, 90, 1558.

Jongpaiboonkit, L., Franklin-Ford, T., Murphy, W. L., Adv. Mater. 2009, 21, 1960-1963.

Kawachi, G., T. Watanabe, K. Kikukta, C. Ohtsuki, Key Eng. Mat. 2008, 361-363, 71.

Kokubo, T.; Ito, S.; Huang, Z. T.; Hayashi, T.; Sakka, S.; Kitsugi, T.; Yamamuro, T., Ca, P-rich layer formed on high-strength bioactive glass-ceramic A-W. Journal of Biomedical Materials Research 1990, 24, (3), 331-43.

Leveque, I.; Cusack, M.; Davis, S. A.; Mann, S., Promotion of fluorapatite crystallization by soluble-matrix proteins from *Lingula anatina* shells. Angewandte Chemie-International Edition 2004, 43, (7), 885-888.

LeGeros, R. Z., Properties of osteoconductive biomaterials: Calcium phosphates. Clinical Orthopaedics and Related Research 2002, 395, 81-98.

Li, P. J.; Ohtsuki, C.; Kokubo, T.; Nakanishi, K.; Soga, N.; Nakamuro, T., Apatite formation induced by silica-gel in a simulated body-fluid. Journal of the American Ceramic Society 1992, 75, (8), 2094-7.

Lin, J. H. C.; Kuo, K. H.; Ding, S. J.; Ju, C. P., Surface reaction of stoichiometric and calcium-deficient hydroxyapatite in simulated body fluid. Journal of Materials Science-Materials in Medicine 2001, 12, (8), 731-41.

Luong, L. N.; Hong, S. I.; Patel, R. J.; Outslay, M. E.; Kohn, D. H., Spatial control of protein within biomimetically nucleated mineral. Biomaterials 2006, 27, (7), 1175-1186.

Mann, S., Biomineralization: Principles and concepts in bioinorganic materials chemistry, Oxford University Press, 2001.

Matsumoto, T., M. Okazaki, M. Inoue, S. Yamaguchi, T. Kusunose, T. Toyonaga, Y. Hamada, J. Takahashi, Biomaterials 2004, 25, 3807.

Meng, F. T., G. H. Ma, W. Qiu, Z. G. Su, J. Control. Release 2003, 91, 407.

Miyaji, F., Kim, H. M., Handa, S., Kokubo, T., Nakamura, T., Bonelike apatite coating on organic polymers. Novel nucleation process using sodium silicate solution. Biomaterials 1999, 20, 913-9.

Moror, A. S., A. Olteanu, G. B. Young, G. J. Pielak, Protein Sci. 2001, 10, 2195.

Mu, L., Feng, S. S., J. Controlled Release 2001, 76, 239.

Murphy, M. B. et al., Biomacromolecules 2007, 8, 2237-2243.

Murphy, W. L., P. B. Messersmith, Polyhedron 2000, 19, 357.

Murphy, W. L., Kohn, D. H.; Mooney, D. J., Growth of continuous bonelike mineral within porous poly(lactide-co-glycolide) scaffolds in vitro. Journal of biomedical Materials Research 2000, 50, 50-8.

Murphy, W. L., Mooney, D. J., Bioinspired growth of crystalline carbonate apatite on biodegradable polymer substrata. Journal of the American Chemical Society 2002, 124, (9), 1910-1917.

Murphy, M. B., J. D. Hartgerink, A. Goepferick, A. G. Mikos, Biomacromolecules 2007, 8, 2237.

Newman, K. D., M. W. McBurney, Biomaterials 2004, 25, 5763.

O'Donnell, P. B., J. W. Mcginity, Adv. Drug Deliver Rev. 1997, 28, 25.

Oyane, A.; Kim, H. M.; Furuya, T.; Kokubo, T.; Miyazaki, T.; Nakamura, T., Preparation and assessment of revised simulated body fluids. Journal of Biomedical Materials Research Part A 2003, 65A, 188-95.

Qui, Q.-Q.; Ducheyne, P.; Ayyaswamy, P. S., New bioactive, degradable composite microspheres as tissue engineering substrates. Journal of Biomedical Materials Research Part A 2000, 52, (1), 66-76.

Pandey, R., G. K. Khuller, Chemotherapy 2007, 53, 437.

Porjazoska, A., K. Goracinova, K. Mladenovska, M. Glavas, M. Simonovska, E. I. Janjevic, M. Cvetkovska, Acta Pharm. 2004, 54, 215.

Raman, C.; Berkland, C.; Kim, K.; Pack, D. W., Modeling small-molecule release from PLG microspheres: effects of polymer degradation and nonuniform drug distribution. Journal of Controlled Release 2005, 103, (1), 149-58.

Ruhe, P. Q., Boerman, 0. C., Russel, F. G. M., Spauwen, P. H. M., Mikos, A. G., Jansen, J. A. J., Controlled Release 2005, 106, 162-171.

Schmaljohann, D., Adv. Drug Deliver Rev. 2006, 58, 1655.

Schroder, E.; Jonsson, T.; Poole, L., Hydroxyapatite chromatography: altering the phosphate-dependent elution profile of protein as a function of pH. Analytical Biochemistry 2003, 313, 176-8.

Su, X.; Sun, K.; Cui, F. Z.; Landis, W. J., Organization of apatite crystals in human woven bone. Bone 2003, 32, 150-62.

Tanahashi, M.; Yao, T.; Kokubo, T.; Minoda, M.; Miyamoto, T.; Nakamura, T.; Yamamuro, T., Apatite coating on organic polymers b a biomimetic process. Journal of the American Ceramic Society 1994, 77, 2805-8.

Uchida, M.; Kim, H. M.; Kokubo, T.; Miyaji, F.; Nakamura, T., Bonelike apatite formation induced on zirconia gel in a simulated body fluid and its modified solutions. Journal of the American Ceramic Society 2001, 84, (9), 2041-4.

Urist, M. R., Y. K. Huo, A. G. Brownell, W. M. Hohl, J. Buyske, A. Lietze, P. Tempst, M. Hunkapiller, R. J. DeLange, P. Natl. Acad. Sci. USA 1984, 81, 371.

Vaupel, P., F. Kallinowski, P. Okunieff, Cancer Res. 1989, 49, 6449.

Yamaguchi, M., A. Igarashi, H. Hisawa, Y. Tsurusaki, J. Cell. Biochem. 2003, 89, 356.

Yamashita, K.; Arashi, T.; Kitagaki, K.; Yamada, S.; Umegaki, T.; Ogawa, K., Preparation of apatite thin-films through Rf-sputtering from calcium-phosphate glasses. Journal of the American Ceramic Society 1994, 77, (2401-7), 2401.

Yang, Y.-Y., T.-S. Chung, N. P. Ng, Biomaterials 2001, 22, 231.

Yokogawa, Y.; Paz Reyes, J.; Mucalo, M. R.; Toriyama, M.; Kawamoto, Y.; Suzuki, T.; Nishizawa, K.; Nagata, F.; Kamayama, T., Growth of calcium phosphate on phosphorylated chitin fibres. Journal of Materials Science: Materials in Medicine 1997, 8, 407-12.

Zhang, R. Y.; Ma, P. X., Biomimetic polymer/apatite composite scaffolds for mineralized tissue engineering. Macromolecular Bioscience 2004, 4, (2), 100-111.

U.S. Patent Application Publication US 2008/0095817 A1.
U.S. Pat. No. 6,767,928 B1.
U.S. Pat. No. 6,541,022 B1.
PCT Publication WO 2008/070355 A2.
PCT Publication WO 2008/082766 A2.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An individual microsphere comprising:
an individual bead comprising a polymer that is negatively charged via a double emulsion process;
a first calcium-containing mineral; and
a first biologically active compound;
wherein the bead comprises a first coating having a first degradation rate, the first coating comprising the first calcium-containing mineral, the first calcium-containing mineral being a carbonated-substituted calcium-deficient hydroxyapatite comprising calcium-phosphate in a molar ratio of 1.4 to 1.6 such that the surface of the first coating contains both positive and negative ions and the positive ions have a release rate of 16 μMol in 25 days and the negative ions have a release rate of 10 μMol in 25 days such that the microsphere has a ζ potential value ranging from −60 mV to −90 mV, and the first biologically active compound is non-covalently attached to the first calcium-containing mineral, wherein the microsphere has a diameter from 0.5 μm to 100 µm and a surface of the individual microsphere comprises porous hydroxyapatite crystals in forms of a plurality of small plates covering the surface of the individual microsphere.

2. The microsphere of claim 1, wherein the polymer
   (i) is bioabsorbable;
   (ii) is a synthetic polymer; or
   (iii) comprises polar oxygen groups.

3. The microsphere of claim 1, wherein the polymer is at least one of a poly(D,L-lactide-co-glycolide) (PLG), a polycarboxylate, a polyanhydride, a poly($\alpha$-hydroxy ester), a poly(ethylene terephthalate), poly(carbonate), a poly(amides), a poly(lactone), a poly(saccharide), a poly(acrylate), and about 85:15 lactide:glycolide.

4. The microsphere of claim 1, wherein the bead is poly(D,L-lactide-co-glycolide) (PLG), wherein the PLG is about 85:15 lactide:glycolide.

5. The microsphere of claim 1, wherein the biologically active compound is at least one of an organic compound less than 2000 MW, an oligopeptide, a polypeptide, and a nucleic acid.

6. The microsphere of claim 5, wherein the organic compound is an antibiotic, a corticosteroid, or a statin.

7. The microsphere of claim 5, wherein the organic compound is cefazolin, cefuroxime, clindamycin, vancomycin, or dexamethasone.

8. The microsphere of claim 5, wherein the oligopeptide or polypeptide is selected from the group consisting of
   (i) a cytokine, an enzyme, or a protein comprising an antibody binding site;
   (ii) an oligopeptide having the amino acid sequence GGRGDSP (SEQ ID NO: 3), GGIKVAV (SEQ ID NO: 4), GGYIGSR (SEQ ID NO: 5), GGDGEA (SEQ ID NO: 6), GGKIPKASSVPTELSAISTLYL (SEQ ID NO: 7), AAAAEPRREVAEL (SEQ ID NO: 1), or AAAA$\gamma$EPRR$\gamma$EVA$\gamma$EL (SEQ ID NO: 2), where $\gamma$E is carboxyglutamate; and
   (iii) a bone morphogenetic protein-2, a bone morphogenetic protein-7, a vascular endothelial growth factor, a fibroblast growth factor-2, a platelet-derived growth factor, a transforming growth factor-beta, an interleukin, or a human growth hormone.

9. The microsphere of claim 5, wherein the nucleic acid is a microRNA, an antisense nucleic acid, or a vector.

10. The microsphere of claim 1, further comprising a second biologically active compound non-covalently adhering to the first calcium-containing mineral.

11. The microsphere of claim 1, wherein the biologically active compound is
    (i) at more than one level of the first calcium-containing mineral; or
    (ii) modified to change the rate at which the biologically active compound is released from the microsphere.

12. The microsphere of claim 11, wherein the biologically active compound further comprises a moiety that increases the strength of binding of the biologically active compound to the first calcium-containing mineral.

13. The microsphere of claim 12, wherein the moiety is a peptide comprising a poly(aspartic acid), a poly(glutamic acid), AAAAEPRREVAEL (SEQ ID NO: 1), or AAAA$\gamma$EPRR$\gamma$EVA$\gamma$EL (SEQ ID NO: 2), where $\gamma$E is carboxyglutamate.

14. The microsphere of claim 1, wherein the biologically active compound is a first biologically active compound and further comprising a second biologically active compound adhering to the first calcium-containing mineral or the first biologically active compound.

15. The microsphere of claim 14, wherein the first biologically active compound and the second biologically active compound are on different levels of the first calcium-containing mineral.

16. The microsphere of claim 1, further comprising an isolated cell.

17. The microsphere of claim 16, wherein the bead is poly(D,L-lactide-co glycolide) (PLG), wherein the PLG is about 85:15 lactide:glycolide.

18. The microsphere of claim 16, wherein the isolated cell is an isolated mammalian cell.

19. The microsphere of claim 16, wherein the microsphere comprises a first binding agent that binds to a second binding agent on the isolated cell.

20. The microsphere of claim 19, wherein the first binding agent is
    (i) a receptor, a first nucleic acid or a cell adhesion peptide; or
    (ii) the cell adhesion peptide GGRGDSP (SEQ ID NO: 3), GGIKVAV (SEQ ID NO: 4), GGYIGSR (SEQ ID NO: 5), or GGDGEA (SEQ ID NO: 6); and the second binding agent is a ligand of the receptor, a second nucleic acid complementary to the first nucleic acid, or a ligand of the cell adhesion peptide.

21. The microsphere of claim 16, further comprising a cytokine that interacts with the isolated cell.

22. The microsphere of claim 1, having a diameter from about 2 µm to about 6 µm.

23. A mineral-coated individual microsphere comprising:
    an individual microsphere being a poly(D,L-lactide-co-glycolide) (PLG), the individual PLG microspheres being synthesized via a double emulsion process and the surface of the individual PLG microsphere includes a negatively charged group and the surface of the individual PLG microsphere comprises porous hydroxyapatite crystals in forms of a plurality of small plates covering the surface of the individual microsphere;
    a carbonated-substituted calcium-deficient hydroxyapatite having nanocyrstallites coated around the PLG microsphere and comprising calcium-phosphate in a molar ratio of 1.4 to 1.6 such that the surface of the individual PLG microsphere contains both positive and negative ions and the positive ions have a release rate of 16 µMol in 25 days and the negative ions have a release rate of about 10 µMol in 25 days such that the microsphere has a $\zeta$ potential value ranging from −60 mV to −90 mV; and
    a biologically active compound non-covalently attached to the carbonated-substituted calcium-deficient hydroxyapatite.

24. A method of treatment in a vertebrate using the microsphere of at least one of claims, 8, 11, 14, 20-22, 24, 28, 30-31, 33-41, 43, or 46.

25. The method of claim 24, wherein the vertebrate is a human.

26. A method of producing a microsphere of claim 1, comprising incubating a bead in a physiological saline solution comprising carbonate, calcium, and phosphate such that a first calcium-containing mineral layer coating forms on the bead, where the bead with the mineral layer coating is the microsphere, and further comprising;
    (i) adding a component that adheres to the first calcium-containing mineral layer to the microsphere, wherein the component introduces a functional group to the first calcium-containing mineral layer; or (ii) incubating the microsphere with a biologically active compound such that the biologically active compound adheres to the microsphere.

27. The method of claim 26, wherein the solution comprises
(i) about 141 mM NaCl, about 4.0 mM KCl, about 1 mM $MgCl_2$, about 0.5 mM $MgSO_4$, about 4.2 mM $NaHCO_3$, Tris, about 5 mM $CaCl_2$, and about 2 mM $KH_2PO_4$; or
(ii) a surfactant.

28. The method of claim 26, wherein
(i) the component is incubated with the microsphere such that the biologically active compound is non-covalently bound to the microsphere;
(ii) further comprising adhering the component to the microsphere such that the component introduces a functional group to the microsphere, then covalently attaching the biologically active compound to the functional group; or
(iii) the biologically active compound is incubated with the bead in the physiological saline solution such that the biologically active compound is deposited on the bead along with the mineral layer coating.

29. The method of claim 24, for treating vertebrate with a tissue defect.

30. The method of claim 27, wherein the surfactant is Tween.

\* \* \* \* \*